United States Patent
Gao et al.

(10) Patent No.: US 11,739,313 B2
(45) Date of Patent: Aug. 29, 2023

(54) METHOD FOR REGULATING GENE EXPRESSION

(71) Applicants: INSTITUTE OF GENETICS AND DEVELOPMENTAL BIOLOGY, CHINESE ACADEMY OF SCIENCES, Beijing (CN); TIANJIN GENOVO BIOTECHNOLOGY CO., LTD., Tianjin (CN)

(72) Inventors: Caixia Gao, Beijing (CN); Huawei Zhang, Shandong Province (CN); Yidong Ran, Tianjin (CN)

(73) Assignees: INSTITUTE OF GENETICS AND DEVELOPMENTAL BIOLOGY, CHINESE ACADEMY OF SCIENCES, Beijing (CN); TIANJIN GENOVO BIOTECHNOLOGY CO., LTD., Tianjin (CN)

( * ) Notice: Subject to any disclaimer, the term of this patent is extended or adjusted under 35 U.S.C. 154(b) by 382 days.

(21) Appl. No.: 16/756,935

(22) PCT Filed: Oct. 19, 2018

(86) PCT No.: PCT/CN2018/110928
§ 371 (c)(1),
(2) Date: Apr. 17, 2020

(87) PCT Pub. No.: WO2019/076355
PCT Pub. Date: Apr. 25, 2019

(65) Prior Publication Data
US 2021/0189375 A1    Jun. 24, 2021

(30) Foreign Application Priority Data
Oct. 19, 2017 (CN) .......................... 201710976945.0

(51) Int. Cl.
| C12N 15/82 | (2006.01) |
| C12N 15/10 | (2006.01) |
| C12N 9/22 | (2006.01) |
| C12N 15/113 | (2010.01) |

(52) U.S. Cl.
CPC ............. *C12N 15/102* (2013.01); *C12N 9/22* (2013.01); *C12N 15/113* (2013.01); *C12N 15/8218* (2013.01); *C12N 2310/20* (2017.05)

(58) Field of Classification Search
CPC combination set(s) only.
See application file for complete search history.

(56) References Cited

FOREIGN PATENT DOCUMENTS

| CN | 101768591 A | 7/2010 |
| CN | 103642931 | 3/2014 |
| CN | 104884622 A | 9/2015 |
| WO | 01/96569 A1 | 12/2001 |
| WO | 02/20789 A1 | 3/2002 |
| WO | 2016/116032 | 7/2016 |

OTHER PUBLICATIONS

Kolli, N. et al. International Journal of Molecular Sciences (Apr. 2017) vol. 118, No. 754, pp. 1-14. (Year: 2017).*
Laing, W.A. et al. (Mar. 2015) The Plant Cell; vol. 27: 772-786. (Year: 2016).*
Mehdi, H. et al. Gene (1990) 173-178. (Year: 1990).*
Laing, W.A. et al. The Plant Cell, vol. 27: 772-786; Mar. 2015. (Year: 2015).*
International Search Report and Written Opinion issued in International Application No. PCT/CN2018/110928 dated Jan. 30, 2019.
Nivya Kolli et al., "CRISPR-Cas9 Mediated Gene-Silencing of the Mutant Huntingtin Gene in an In Vitro Model of Huntington's Disease", International Journal of Molecular Sciences, vol. 18, No. 4, Apr. 2, 2017 (Apr. 2, 2017).
Shan, Q. et al. "Targeted genome modification of crop plants using a CRISPR-Cas system", Nat. Biotechnol. 31, 686-688 (2013).
Tang et al., "A CRISPR-Cpf1 system for efficient genome editing and transcriptional repression in plants," Nature Plants 3, 17018 (2017), 5 pages.
Seth and Harish, "Current status of potential applications of repurposed Cas9 for structural and functional genomics of plants," Biochemical and Biophysical Research Communications, vol. 480, Issue 4, Nov. 25, 2016, pp. 499-507.
Zong et al., "Precise base editing in rice, wheat and maize with a Cas9-cytidine deaminase fusion," Nat Biotechnol 35, 438-440 (2017).
Shukla et al., "Precise genome modification in the crop species *Zea mays* using zinc-finger nucleases," Nature 459, 437-441 (2009).
Townsend et al., "High-frequency modification of plant genes using engineered zinc-finger nucleases," Nature 459, 442-445 (2009).
Li et al., "High-efficiency TALEN-based gene editing produces disease-resistant rice," Nat Biotechnol 30, 390-392 (2012).
Hanfrey et al., "Abrogation of Upstream Open Reading Frame-mediated Translational Control of a Plant S-Adenosylmethionine Decarboxylase Results in Polyamine Disruption and Growth Peturbations", Journal of Biological Chemistry, 2002, vol. 277, No. 46, pp. 44131-44139.
Imai et al., "The dwarf phenotype of the *Arabidopsis* acl5 mutant is suppressed by a mutation in an upstream ORF of a bHLH gene", Development, 2006, vol. 133, No. 18, pp. 3575-3585.
Guerrero-Gonzalez et al., "*Arabidopsis* Polyamine oxidase-2 uORF is required for downstream translational regulation", Plant Physiology and Biochemistry, 2016, vol. 108, pp. 381-390.
Schwanhausser et al., "Global quantification of mammalian gene expression control", Nature, 2011, vol. 473, pp. 337-342.
Calvo et al., "Upstream open reading frames cause widespread reduction of protein expression and are polymorphic among humans", PNAS, 2009, vol. 106, No. 18, pp. 7507-7512.

(Continued)

*Primary Examiner* — Russell Kallis
(74) *Attorney, Agent, or Firm* — Troutman Pepper Hamilton Sanders LLP

(57) ABSTRACT

A method of modifying an upstream open reading frame (uORF) by genome editing technique to regulate gene expression.

5 Claims, 14 Drawing Sheets
Specification includes a Sequence Listing.

(56) References Cited

OTHER PUBLICATIONS

Von Arnim et al., "Regulation of plant translation by upstream open reading frames", Plant Science, 2014, vol. 214, pp. 1-12.
Hellens et al., "Transient expression vectors for functional genomics, quantification of promoter activity and RNA silencing in plants", Plant Methods, 2005, vol. 1, No. 13, 14 pages.
Kawakami et al., "TTG as the Initiation Codon of *Salmonella* slyA, a Gene Required for Survival within Macrophages", Microbiol Immunol., 1999, vol. 43, No. 4, pp. 351-357.
Mehdi et al., "Initiation of translation at CUG, GUG, and ACG codons in mammalian cells", Gene, 1990, vol. 91, pp. 173-178.
Laing et al.,"An Upstream Open Reading Frame Is Essential for Feedback Regulation of Ascorbate Biosynthesis In *Arabidopsis*", The Plant Cell, 2015, vol. 27, pp. 772-786.
Bulley et al., "Enhancing ascorbate in fruits and tubers through over-expression of the L-galactose pathway gene GDP-L-galactose phosphorylase", Plant Biotechnology Journal, 2012, vol. 10, pp. 390-397.
Zhou et al., "Engineering ascorbic acide biosynthetic pathway in *Arabidopsis* leaves by single and double gene transformation", Biologica Plantarum, 2012, vol. 56, No. 3, pp. 451-457.
Reyes-Chin-Wo et al., "Genome assembly with in vitro proximity ligation data and whole-genome triplication in lettuce", Nature Communications, 2017, vol. 8, Article 14953, 11 pages.
Zhang et al., "Efficient and transgene-free genome editing in wheat through transient expression of CRISPR/Cas9 DNA or RNA", Nature Communications, 2016, vol. 7, Article 12617, 8 pages.
Liang et al., "Efficient DNA-Free genome editing of bread wheat using CR1SPR/Cas9 ribonucleoprotein complexes", Nature Communications, 2017, vol. 8, Article 14261, 5 pages.
Yan et al., "High-Efficiency Genome Editing in *Arabidopsis* Using YAO Promoter-Driven CRISPR/Cas9 System", Molecular Plant, 2015, vol. 8, pp. 1820-1823.
Xing et al., "A CRISPR/Cas9 toolkit for multiplex genome editing in plants", BMC Plant Biology, 2014, vol. 14, No. 327, 12 pages.
Zhai et al., "Isolation of Protoplasts from Tissues of 14-day-old Seedlings of *Arabidopsis thaliana*", Journal of Visualized Experiments, 2009, 30, pii: 1149. doi: 10.3791/1149.
Yoo et al., "*Arabidopsis* mesophyll protoplasts: a versatile cell system for transient gene expression analysis", Nature Protocols, 2007, vol. 2, No. 7, pp. 1565-1572.
Cui et al., "*Arabidopsis* Ubiquitin Conjugase UBC32 Is an ERAD Component That Functions in Brassinosteroid-Mediated Salt Stress Tolerance", The Plant Cell, 2012, vol. 24, pp. 233-244.
Zhang et al., "The RING Finger Ubiquitin E3 Ligase SDIR1 Targets SDIR1-Interacting Protein1 for Degradation to Modulate the Salt Stress Response and ABA Signaling in *Arabidopsis*", The Plant Cell, 2015, vol. 27, pp. 214-227.
Kovács et al., "Quantitative Determination of Ascorbate from the Green Alga *Chlamydomonas reinhardtii* by HPLC", Bio-protocol, 2016, vol. 6, Issue 24, e2067, 7 pages.
Liang et al., "Translation efficiency of mRNAs is Increased by antisense oligonucleotides targeting upstream open reading frames", Nature Biotechnology, 2016, vol. 34, No. 8, pp. 875-882.
Xu et al., "Global translational reprogramming is a fundamental layer of immune regulation in plants", Nature, 2017, vol. 545, pp. 487-490.
Wang et al., "BRI1 is a critical component of a plasma-membrane receptor for plant steroids", Letters to Nature, 2001, vol. 410, pp. 380-383.
Woo et al., "DNA-free genome editing in plants with preassambled CRISPR-Cas9 ribonucleoproteins", Nature Biotechnology, 2015, vol. 33, No. 11, pp. 1162-1164.

\* cited by examiner

Figure 3

```
AtVTC2    MLKIKRVPTVVSNYQKDDGA--EDPVGCGRNCLGACCLNGARLPLYACKNLVKSGEKLVI
LsGGP1    MLRIKRVPTVLSNYQKEESEDAGATGGCGRNCMRDCCLPGAKLPLYAFRKSDK------VE
LsGGP2    MLRIKRVPTILSNYQKEGVEEGGAARGCGRNCLRNCCLTGAKLPLYAFPKSNK------VD
          **:******::****:       ******:  *** **:*****  : *    *

AtVTC2    SHEAIEPPVAFLESLVLGEWEDRFQRGLFRYDVTACETKVIPGKYGFVAQLNEGRHLKKR
LsGGP1    SSDKKEPPFAFLDSLLLGEWEDRVERGLFRYDVTACETKVIPGDYGFVAQLNEGRHLKKR
LsGGP2    LCHNNEAPFAFLDSLLLGEWEERMERGLFRYDVTACATKVIPGELGFVAQLNEGRHLKKR
            * *.***:**:*****:*.:********** *****.  **********.*****

AtVTC2    PTEFRVDKVLQSFDGSKFNFTKVGQEELLFQFEAGEDAQVQFFPCMPIDPENSPSVVAIN
LsGGP1    PTEFRVDKVLQPFDRSKFNFTKVGQEEILFQFESSEDDEVKFYPNAPVNINNSPSVVAIN
LsGGP2    PTEFRVDKVLQPFDENKFNFTKVGQEEVLFQFEASEDGEVQFHPNAPINVDGSPSVVAIN
          ********** ** .***********:*****::** :*:*.*  *::  :.*******

AtVTC2    VSPIEYGHVLLIPRVLDCLPQRIDHKSLLLAVHMAAEAANPYFRLGYNSLGAFATINHLH
LsGGP1    VSPIEYGHVLLIPRILECLPQRIDHESFLLALYMASEAGNPYFRVGYNSLGAFATINHLH
LsGGP2    VSPIEYGHVLLIPRILERLPQRIDHESLLLALYMAREAGSQYFRLGYNSLGAFATINHLH
          **************:*: *******:****:*** **.. ***:****************

AtVTC2    FQAYYLAMPFPLEKAPTKKITTTV---------SGVKISELLSYPVRSLLFEGG--SSMQE
LsGGP1    FQAYYLAVTFPIEKAPTRKITDFN---------GGVVISEILKYPVRGLVFEGG--YSLED
LsGGP2    FQAYYLGLPFPIEKAPTRKITDFNGNGNGNDNGGVVISEILNYPVRGLVYEGGSGSSLED
          ******.: **:*****:***            .** ***:*.****.*::***   *:::

AtVTC2    LSDTVSDCCVCLQNNNIPFNILISDCGRQIFLMPQCYAEKQALGEVSPEVLETQVNPAVW
LsGGP1    LSNVVSDSCMCLQDNNIPYNVLISDSGRRIFLLPQCYAEKQALGEVSSELLDTQVNPAVW
LsGGP2    LSNAVADSCICLQDNNIPYNVLISDSGRRIFVLPQCYAEKQALGEVSGELLDTQVNPAVW
          **:..*:*.*:***:****:*****.***:**:**********: *:*:*******

AtVTC2    EISGHMVLKRKEDYEGASEDNAWRLLAEASLSEERFKEVTALAFEAIGCSNQEEDLEGTI
LsGGP1    EISGHMVLKRKEDYDGASEENAWRLLAEVSLSEERFQEVIAIIFEAISCAVVVTEA-GSL
LsGGP2    EISGHMVLKRKEDYEGASEEKAWRLLAEVSLSEERFQEVVAIIFEAISITEKMLTE-----
          **************:*****:*******.*******:**:*: ****.  :

AtVTC2    VHQQ---NSSGNVNQKSNRTHGGPITNGT----AAECLVLQ
LsGGP1    GDEDELRDVEDVDQVRDVDGSGSHKAGIVAGKQECMVQH
LsGGP2    ------------DEQDVDQ-----V-DGGPREAAMAPGNQECLVQY
                    .:*:*     .*   .    **:*
```

Figure 5 a

**HindIII-*p35S:AtBRI1*-5'-leader sequence (BRI1-uORF)-NcoI**

AAGCTTGTACCCCTACTCCAAAAATGTCAAAGATACAGTCTCAGAAGACCAAAGGGCTATTGAGA
CTTTTCAACAAAGGGTAATTTCGGGAAACCTCCTCGGATTCCATTGCCCAGCTATCTGTCACTTC
ATCGAAAGGACAGTAGAAAAGGAAGGTGGCTCCTACAAATGCCATCATTGCGATAAAGGAAAGGC
TATCATTCAAGATGCCTCTGCCGACAGTGGTCCCAAAGATGGACCCCCACCCACGAGGAGCATCG
TGGAAAAAGAAGACGTTCCAACCACGTCTTCAAAGCAAGTGGATTGATGTGACATCTCCACTGAC
GTAAGGGATGACGCACAATCCCACTATCCTTCGCAAGACCCTTCCTCTATATAAGGAAGTTCATT
TCATTTGGAGAGGACGTCTTTTGACTCTCTCTCTCTCTCCTCTCTTTCTGCTTTCCTCAATCTC
TCTCTTCTATCTCTAGAGCTTCCACTTCCTCTCTAATGGTGGAACCAAAACCCTAGATTCCCCC
TTCATCTTTCTACTTCCCACACTTTCTCTCTCACAAACTCTTGAGAACCATGG b

**HindIII-*p35S:AtBRI1*-5'-leader sequence (uATG→AAA)-NcoI**

AAGCTTGTACCCCTACTCCAAAAATGTCAAAGATACAGTCTCAGAAGACCAAAGGGCTATTGAGA
CTTTTCAACAAAGGGTAATTTCGGGAAACCTCCTCGGATTCCATTGCCCAGCTATCTGTCACTTC
ATCGAAAGGACAGTAGAAAAGGAAGGTGGCTCCTACAAATGCCATCATTGCGATAAAGGAAAGGC
TATCATTCAAGATGCCTCTGCCGACAGTGGTCCCAAAGATGGACCCCCACCCACGAGGAGCATCG
TGGAAAAAGAAGACGTTCCAACCACGTCTTCAAAGCAAGTGGATTGATGTGACATCTCCACTGAC
GTAAGGGATGACGCACAATCCCACTATCCTTCGCAAGACCCTTCCTCTATATAAGGAAGTTCATT
TCATTTGGAGAGGACGTCTTTTGACTCTCTCTCTCTCTCCTCTCTTTCTGCTTTCCTCAATCTC
TCTCTTCTATCTCTAGAGCTTCCACTTCCTCTCTAAAAGTGGAACCAAAACCCTAGATTCCCCC
TTCATCTTTCTACTTCCCACACTTTCTCTCTCACAAACTCTTGAGAACCATGG c

**HindIII-*p35S:AtBRI1*-5'-leader sequence(*uorf-1*:uATG→AGTG)-NcoI**

AAGCTTGTACCCCTACTCCAAAAATGTCAAAGATACAGTCTCAGAAGACCAAAGGGCTATTGAGA
CTTTTCAACAAAGGGTAATTTCGGGAAACCTCCTCGGATTCCATTGCCCAGCTATCTGTCACTTC
ATCGAAAGGACAGTAGAAAAGGAAGGTGGCTCCTACAAATGCCATCATTGCGATAAAGGAAAGGC
TATCATTCAAGATGCCTCTGCCGACAGTGGTCCCAAAGATGGACCCCCACCCACGAGGAGCATCG
TGGAAAAAGAAGACGTTCCAACCACGTCTTCAAAGCAAGTGGATTGATGTGACATCTCCACTGAC
GTAAGGGATGACGCACAATCCCACTATCCTTCGCAAGACCCTTCCTCTATATAAGGAAGTTCATT
TCATTTGGAGAGGACGTCTTTTGACTCTCTCTCTCTCTCCTCTCTTTCTGCTTTCCTCAATCTC
TCTCTTCTATCTCTAGAGTTCCACTTCCTCTCTAAGTGGTGGAACCAAAACCCTAGATTCCCC
CTTCATCTTTCTACTTCCCACACTTTCTCTCTCACAAACTCTTGAGAACCATGG d

**HindIII-*p35S:AtBRI1*-5'-leader sequence(*uorf-2*:uATG→ATTG)-NcoI**

AAGCTTGTACCCCTACTCCAAAAATGTCAAAGATACAGTCTCAGAAGACCAAAGGGCTATTGAGA
CTTTTCAACAAAGGGTAATTTCGGGAAACCTCCTCGGATTCCATTGCCCAGCTATCTGTCACTTC
ATCGAAAGGACAGTAGAAAAGGAAGGTGGCTCCTACAAATGCCATCATTGCGATAAAGGAAAGGC
TATCATTCAAGATGCCTCTGCCGACAGTGGTCCCAAAGATGGACCCCCACCCACGAGGAGCATCG
TGGAAAAAGAAGACGTTCCAACCACGTCTTCAAAGCAAGTGGATTGATGTGACATCTCCACTGAC
GTAAGGGATGACGCACAATCCCACTATCCTTCGCAAGACCCTTCCTCTATATAAGGAAGTTCATT
TCATTTGGAGAGGACGTCTTTTGACTCTCTCTCTCTCTCCTCTCTTTCTGCTTTCCTCAATCTC
TCTCTTCTATCTCTAGAGCTTCCACTTCCTCTCTAATTGGTGGAACCAAAACCCTAGATTCCCC
CTTCATCTTTCTACTTCCCACACTTTCTCTCTCACAAACTCTTGAGAACCATGG

Figure 8 e

**HindIII-*p35S:AtVTC2*-5'-leader sequence (VTC2-uORF)-NcoI**
AAGCTTGTACCCCTACTCCAAAAATGTCAAAGATACAGTCTCAGAAGACCAAAGGGCTATTGAGA
CTTTTCAACAAAGGGTAATTTCGGGAAACCTCCTCGGATTCCATTGCCCAGCTATCTGTCACTTC
ATCGAAAGGACAGTAGAAAAGGAAGGTGGCTCCTACAAATGCCATCATTGCCGATAAAGGAAAGGC
TATCATTCAAGATGCCTCTGCCGACAGTGGTCCCAAAGATGGACCCCCACCCACGAGGAGCATCG
TGGAAAAAGAAGACGTTCCAACCACGTCTTCAAAGCAAGTGGATTGATGTGACATCTCCACTGAC
GTAAGGGATGACGCACAATCCCACTATCCTTCGCAAGACCCTTCCTCTATATAAGGAAGTTCATT
TCATTTGGAGAGGACGTATCATCAAAAACACCTCAAAGAATTATTCATTCAGGCATCTTCTCAA
ATTTTGTTTGTGAAAAAACCCACATCAAAAGATCTCTCATTTATTCGTTTCGTTTCTGCTGTT
TTGAGTGTCGGTTCGTTTTAGCTGTAATCTTTTTTCCGGCGTTCGATTGAAAAATCCGGGC
AACAGCTGATCGAATCACGGCTATACACGGGATATCACGGGGTGTTAGCTCACATGTCCATATT
GTCCGACAGAAGGGTTGTTTAATCGAAACTAATCCTTTGCCGCACGGAGGACGTGGAGCTCTGCC
GTCTGAAGGCGGCAGCCCTTCCGATCTCCTCTTTCTCGCCGGTGGCGGTTCCAGCTTTAACTTCT
TTTCCTTTAGGTTTTAGGACTTAGGGTTTGTTAGTGTTTTTCCTTCTCTTTTTTGGTGCTCC
TCAATCGCTTTTCTTGGGGAAGTTTTTCTTTTGCTCTTGAAATTGTCTTTTTGAGACC
ATGG f

**HindIII-*p35S:AtVTC2*-5'-leader sequence (VTC2-uorf:-37bp)-NcoI**
AAGCTTGTACCCCTACTCCAAAAATGTCAAAGATACAGTCTCAGAAGACCAAAGGGCTATTGAGA
CTTTTCAACAAAGGGTAATTTCGGGAAACCTCCTCGGATTCCATTGCCCAGCTATCTGTCACTTC
ATCGAAAGGACAGTAGAAAAGGAAGGTGGCTCCTACAAATGCCATCATTGCCGATAAAGGAAAGGC
TATCATTCAAGATGCCTCTGCCGACAGTGGTCCCAAAGATGGACCCCCACCCACGAGGAGCATCG
TGGAAAAAGAAGACGTTCCAACCACGTCTTCAAAGCAAGTGGATTGATGTGACATCTCCACTGAC
GTAAGGGATGACGCACAATCCCACTATCCTTCGCAAGACCCTTCCTCTATATAAGGAAGTTCATT
TCATTTGGAGAGGACGTATCATCAAAAACACCTCAAAGAATTATTCATTCAGGCATCTTCTCAA
ATTTTGTTTGTGAAAAAACCCACATCAAAAGATCTCTCATTTATTCGTTTCGTTTCTGCTGTT
TTGAGTGTCGGTTCGTTTTAGCTGTAATCTTTTTTCCGGGCTCACGGCTATACACGGGATATC
ACGGGTGTTAGCTCACATGTCCATATTGTCCGACAGAAGGGTTGTTTAATCGAAACTAATCCTT
TGCCGCACGGAGGACGTGGAGCTCTGCCGTCTGAAGGCGGCAGCCCTTCCGATCTCCTCTTTCTC
GCCGGTGGCGGTTCCAGCTTTAACTTCTTTTCCTTTAGGTTTTAGGACTTAGGGTTTGTTAGTGT
TTTTCCTTCTCTTTTTTGGTGCTCTTGAATCGCTTTTCTTGGGGAAGTTTTTCTTTTG
CTCTTGAAATTGTCTTTTTGAGACCATGG g

**HindIII-*p35S:AtVTC2*-5'-leader sequence (VTC2-uorf:-9/+1bp)-NcoI**
AAGCTTGTACCCCTACTCCAAAAATGTCAAAGATACAGTCTCAGAAGACCAAAGGGCTATTGAGA
CTTTTCAACAAAGGGTAATTTCGGGAAACCTCCTCGGATTCCATTGCCCAGCTATCTGTCACTTC
ATCGAAAGGACAGTAGAAAAGGAAGGTGGCTCCTACAAATGCCATCATTGCCGATAAAGGAAAGGC
TATCATTCAAGATGCCTCTGCCGACAGTGGTCCCAAAGATGGACCCCCACCCACGAGGAGCATCG
TGGAAAAAGAAGACGTTCCAACCACGTCTTCAAAGCAAGTGGATTGATGTGACATCTCCACTGAC
GTAAGGGATGACGCACAATCCCACTATCCTTCGCAAGACCCTTCCTCTATATAAGGAAGTTCATT
TCATTTGGAGAGGACGTATCATCAAAAACACCTCAAAGAATTATTCATTCAGGCATCTTCTCAA
ATTTTGTTTGTGAAAAAACCCACATCAAAAGATCTCTCATTTATTCGTTTCGTTTCTGCTGTT
TTGAGTGTCGGTTCGTTTTAGCTGTAATCTTTTTTCCGGCGTTCGATTGAAAAATCCGGGC

Figure 8 (Continued)

a
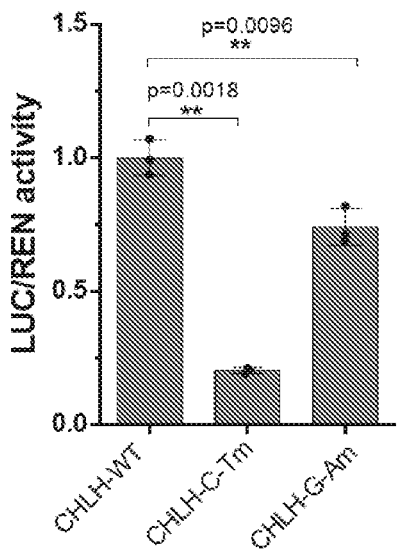
b
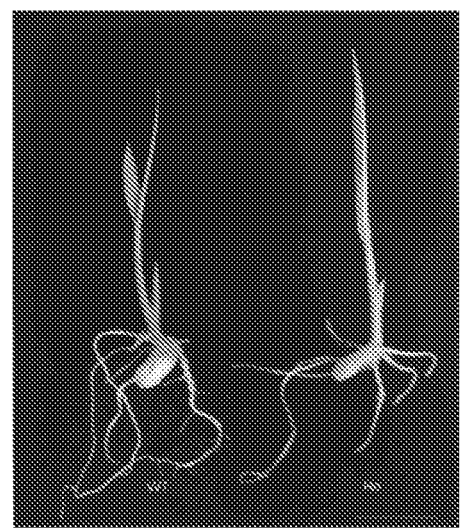
c
5'-leader sequence
GTGTCGCGGCTTTCCGCCACCAAATCGATACGGAACCCGGCGCGCATCCGGTCCTCTCGTCGAGGCGAGAGGAACCTATAC
ATTCGCCACACTCCCCTGCTTCGCTTGCTTGCCCTCCTCTTGCGTAGGGAAAAGGAAGAACACAAGAGCAAGCGAGAGCCC
AGAAATCCTATCCTCGACTGGAGGTTTTTGTGTATTGTATAGTGGTAGATTTTTTTACTGACTTGGGAGTTGTGTGATAGT
GTGGGTTGCGTTCTTTTTTTAGTGTGTAAACG
Figure 9 a b

5'-leader sequence
TCCCGTCGTCCACGCCTCCGCTCCCCCTTCCTCCTCCTCCTCCCCTCCTCCCCTCGCAAACGCAACCTTCTCTCGCCGAAG
AGGGAGAAGGGAAAAGGGGTTTCGATTTCTCCGCGATTTCCCCGCGGATTCCTCCCCCACCGCCTCGATCGAGCTCGCGC
GCGGCCCCCCCGGATTCGGTTCATCCCCCTCCCATCCCCCCGTCTGAGAAGC a
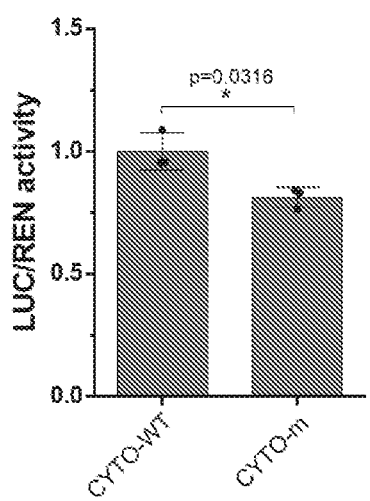
b
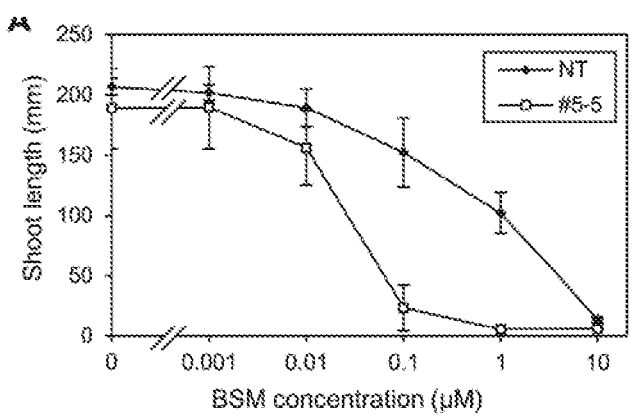
c
5'-leader sequence
GGCTGCGTGACTGTGTCTGCGTCGCGTCTCCTCCACTTTTAAAACCCCAACGACGCTCGATCCGAGATTAATTGTGCTCATA
CTGTTCGACGAATTGACACCATCTGCACACCTGCACCTGCACCTGCACGGCCGTGGCTGTGGACTTGCAGTTGGAGCTAGT
AGCTAGCTCGGGGAGTAGTAGCTAGGTGTAGTTCATCGGATCAAGGGGGGG
Figure 11

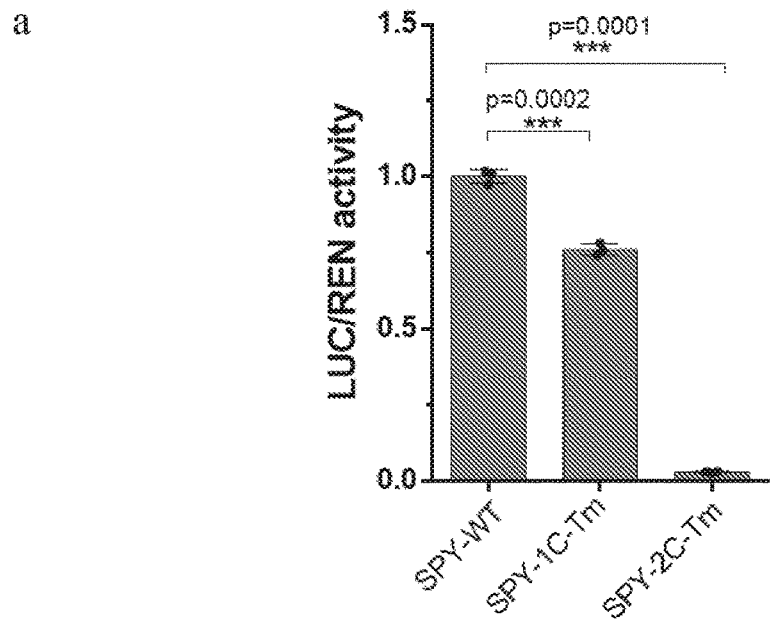

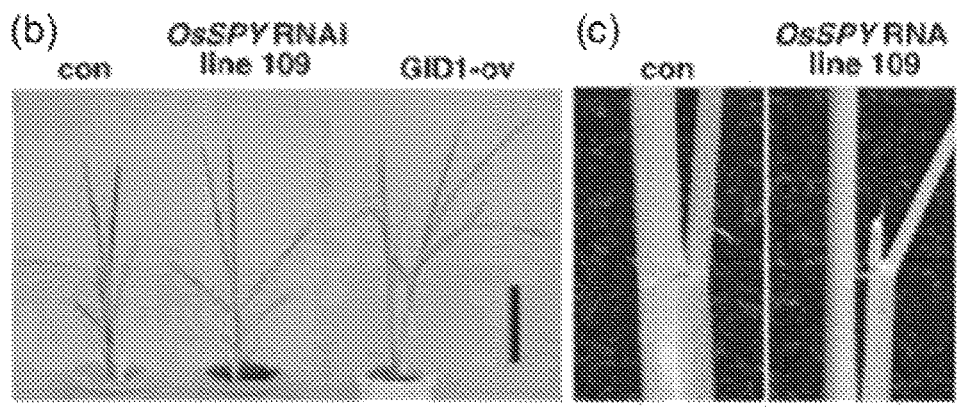

d  5'-leader sequence

TGTAAAGAAGGGAAAAAAAATACGAAAAGCAAAAAGGAATAA
ACGGAGGGGGCTAAACACCAAAATTCCCCCTCTCCTTCTCCTTCCCCTCCTCCCGAAACCCTCGCCGCCGTCGCTGTCG
AAACCCTCGCTGCTGCTGCTGCCGCACGGCGCGGCGGGGTACCGGGTCCCCCTCCCTGCGGCGGCGCGGAGGGGTA
GGTCTCCCCCCCCTCGCTGCGGCGTGGCGGTGGGGGGTGCGGTGCCGGCTGCCGCGCCATGATCTTGCGCCGGTGGA
CTGCGCCTATCCAAT

Figure 12 a

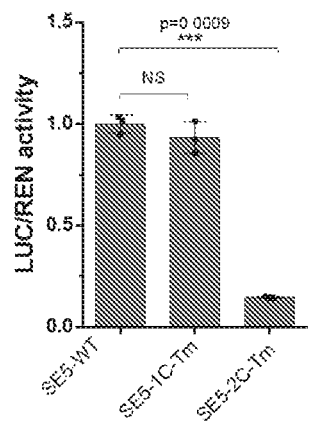

b

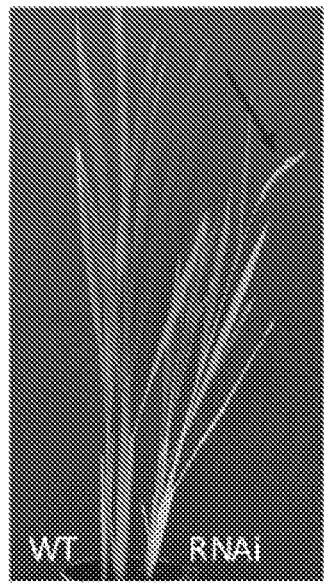

c
5'-leader sequence
GTCGTCTTCCTCCTCGAGACGCCATTGCTGCCGAGGTTGCTTGCCATTCCCGGCCATTCCAATC
CACTCCCACCACCAAGCGCGAGCTCGATTATTTTTTTAATCGATTTTCTCCGATTTAATCCGTAG
AAAATTCCCCACTCCTCCTCCTCCTCCACCGCCGCCGCCGACGCCGCACTCCTCACTCCGCAGA
AGCAACACCAACGCCGCACTCCAACGCCAACCGCCTCCGCGCGCGGCCCGTCGCCATCGTCG
AGCACCTTCACGCTTCCTCCTCCCCCGCACGGAACGGAGACCCCTAGCGCCGCTATAAGAGG
GAGAGAGGTGGGCGGGACTC

SEQUENCE LISTING

```
<160> NUMBER OF SEQ ID NOS: 40

<210> SEQ ID NO 1
<211> LENGTH: 23
<212> TYPE: DNA
<213> ORGANISM: Artificial Sequence
<220> FEATURE:
<223> OTHER INFORMATION: AtBRI1 Target sequence

<400> SEQUENCE: 1
ttccacttcc tctctaatgg tgg                                            23

<210> SEQ ID NO 2
<211> LENGTH: 23
<212> TYPE: DNA
<213> ORGANISM: Artificial Sequence
<220> FEATURE:
<223> OTHER INFORMATION: AtVTC2 Target sequence

<400> SEQUENCE: 2
ggaacaggtg atcggaatca cgg                                            23

<210> SEQ ID NO 3
<211> LENGTH: 22
<212> TYPE: DNA
<213> ORGANISM: Artificial Sequence
<220> FEATURE:
<223> OTHER INFORMATION: LsGGP1 Target sequence
```

<400> SEQUENCE: 3
ccacggctat acacggagca ca                                              22

<210> SEQ ID NO 4
<211> LENGTH: 22
<212> TYPE: DNA
<213> ORGANISM: Artificial Sequence
<220> FEATURE:
<223> OTHER INFORMATION: LsGGP2 Target sequence

<400> SEQUENCE: 4
cgacaagttg cagacatcac gg                                              22

<210> SEQ ID NO 5
<211> LENGTH: 24
<212> TYPE: DNA
<213> ORGANISM: Artificial Sequence
<220> FEATURE:
<223> OTHER INFORMATION: AtBRI1 Oligo-F

<400> SEQUENCE: 5
attgttccac ttcctctcta atgg                                            24

<210> SEQ ID NO 6
<211> LENGTH: 24
<212> TYPE: DNA
<213> ORGANISM: Artificial Sequence
<220> FEATURE:
<223> OTHER INFORMATION: AtVTC2 Oligo-F

<400> SEQUENCE: 6
attgggaaca ggtgatcgga atca                                            24

<210> SEQ ID NO 7
<211> LENGTH: 23
<212> TYPE: DNA
<213> ORGANISM: Artificial Sequence
<220> FEATURE:
<223> OTHER INFORMATION: LsGGP1 Oligo-F

<400> SEQUENCE: 7
attgtgtgct ccgtgtatag ccg                                             23

<210> SEQ ID NO 8
<211> LENGTH: 23
<212> TYPE: DNA
<213> ORGANISM: Artificial Sequence
<220> FEATURE:
<223> OTHER INFORMATION: LsGGP2 Oligo-F

<400> SEQUENCE: 8
attgcgacaa gttgcagaca tca                                             23

<210> SEQ ID NO 9
<211> LENGTH: 24
<212> TYPE: DNA
<213> ORGANISM: Artificial Sequence
<220> FEATURE:
<223> OTHER INFORMATION: AtBRI1 Oligo-R

<400> SEQUENCE: 9
aaacccatta gagaggaagt ggaa                                            24

<210> SEQ ID NO 10

```
<211> LENGTH: 24
<212> TYPE: DNA
<213> ORGANISM: Artificial Sequence
<220> FEATURE:
<223> OTHER INFORMATION: AtVTC2 Oligo-R

<400> SEQUENCE: 10
aaactgattc cgatcacctg ttcc                                              24

<210> SEQ ID NO 11
<211> LENGTH: 23
<212> TYPE: DNA
<213> ORGANISM: Artificial Sequence
<220> FEATURE:
<223> OTHER INFORMATION: LsGGP1 Oligo-R

<400> SEQUENCE: 11
aaaccggcta tacacggagc aca                                               23

<210> SEQ ID NO 12
<211> LENGTH: 23
<212> TYPE: DNA
<213> ORGANISM: Artificial Sequence
<220> FEATURE:
<223> OTHER INFORMATION: LsGGP2 Oligo-R

<400> SEQUENCE: 12
aaactgatgt ctgcaacttg tcg                                               23

<210> SEQ ID NO 13
<211> LENGTH: 22
<212> TYPE: DNA
<213> ORGANISM: Artificial Sequence
<220> FEATURE:
<223> OTHER INFORMATION: qPCR-LUC-F

<400> SEQUENCE: 13
ggattacaag attcaaagtg cg                                                22

<210> SEQ ID NO 14
<211> LENGTH: 20
<212> TYPE: DNA
<213> ORGANISM: Artificial Sequence
<220> FEATURE:
<223> OTHER INFORMATION: qPCR-LUC-R

<400> SEQUENCE: 14
tgatacctgg cagatggaac                                                   20

<210> SEQ ID NO 15
<211> LENGTH: 24
<212> TYPE: DNA
<213> ORGANISM: Artificial Sequence
<220> FEATURE:
<223> OTHER INFORMATION: qPCR-REN-F

<400> SEQUENCE: 15
catgggatga atggcctgat attg                                              24

<210> SEQ ID NO 16
<211> LENGTH: 23
<212> TYPE: DNA
<213> ORGANISM: Artificial Sequence
<220> FEATURE:
<223> OTHER INFORMATION: qPCR-REN-R

<400> SEQUENCE: 16
```

```
gataatgttg gacgacgaac ttc                                          23
```

<210> SEQ ID NO 17
<211> LENGTH: 25
<212> TYPE: DNA
<213> ORGANISM: Artificial Sequence
<220> FEATURE:
<223> OTHER INFORMATION: BRI1-F1

<400> SEQUENCE: 17

```
aagtaggata tgtagcttgc agaag                                        25
```

<210> SEQ ID NO 18
<211> LENGTH: 21
<212> TYPE: DNA
<213> ORGANISM: Artificial Sequence
<220> FEATURE:
<223> OTHER INFORMATION: BRI1-R1

<400> SEQUENCE: 18

```
agatccagaa cttccaagct g                                            21
```

<210> SEQ ID NO 19
<211> LENGTH: 20
<212> TYPE: DNA
<213> ORGANISM: Artificial Sequence
<220> FEATURE:
<223> OTHER INFORMATION: BRI1-RNA-F

<400> SEQUENCE: 19

```
ttggttcttg ctccggtctg                                              20
```

<210> SEQ ID NO 20
<211> LENGTH: 22
<212> TYPE: DNA
<213> ORGANISM: Artificial Sequence
<220> FEATURE:
<223> OTHER INFORMATION: BRI1-RNA-R

<400> SEQUENCE: 20

```
cgtctccact gattttgttt cc                                           22
```

<210> SEQ ID NO 21
<211> LENGTH: 20
<212> TYPE: DNA
<213> ORGANISM: Artificial Sequence
<220> FEATURE:
<223> OTHER INFORMATION: Actin2-F

<400> SEQUENCE: 21

```
gcaccctgtt cttcttaccg                                              20
```

<210> SEQ ID NO 22
<211> LENGTH: 20
<212> TYPE: DNA
<213> ORGANISM: Artificial Sequence
<220> FEATURE:
<223> OTHER INFORMATION: Actin2-R

<400> SEQUENCE: 22

```
aaccctcgta gattggcaca                                              20
```

<210> SEQ ID NO 23
<211> LENGTH: 21
<212> TYPE: DNA

```
<213> ORGANISM: Artificial Sequence
<220> FEATURE:
<223> OTHER INFORMATION: F1

<400> SEQUENCE: 23
ccagtcacga cgttgtaaaa c                                               21

<210> SEQ ID NO 24
<211> LENGTH: 22
<212> TYPE: DNA
<213> ORGANISM: Artificial Sequence
<220> FEATURE:
<223> OTHER INFORMATION: R1

<400> SEQUENCE: 24
caatgaattt cccatcgtcg ag                                              22

<210> SEQ ID NO 25
<211> LENGTH: 22
<212> TYPE: DNA
<213> ORGANISM: Artificial Sequence
<220> FEATURE:
<223> OTHER INFORMATION: F2

<400> SEQUENCE: 25
ctcgaggaag cttctagatt tc                                              22

<210> SEQ ID NO 26
<211> LENGTH: 23
<212> TYPE: DNA
<213> ORGANISM: Artificial Sequence
<220> FEATURE:
<223> OTHER INFORMATION: R2

<400> SEQUENCE: 26
gatccttgta gtctccgtcg tgg                                             23

<210> SEQ ID NO 27
<211> LENGTH: 21
<212> TYPE: DNA
<213> ORGANISM: Artificial Sequence
<220> FEATURE:
<223> OTHER INFORMATION: F3

<400> SEQUENCE: 27
catccagaaa gcccaggtgt c                                               21

<210> SEQ ID NO 28
<211> LENGTH: 19
<212> TYPE: DNA
<213> ORGANISM: Artificial Sequence
<220> FEATURE:
<223> OTHER INFORMATION: R3

<400> SEQUENCE: 28
cagggtaatc tcggtcttg                                                  19

<210> SEQ ID NO 29
<211> LENGTH: 21
<212> TYPE: DNA
<213> ORGANISM: Artificial Sequence
<220> FEATURE:
<223> OTHER INFORMATION: F4

<400> SEQUENCE: 29
catcatggaa agaagcagct t                                               21
```

<210> SEQ ID NO 30
<211> LENGTH: 24
<212> TYPE: DNA
<213> ORGANISM: Artificial Sequence
<220> FEATURE:
<223> OTHER INFORMATION: R4

<400> SEQUENCE: 30
gaattcccga tctagtaaca taga                                          24

<210> SEQ ID NO 31
<211> LENGTH: 23
<212> TYPE: DNA
<213> ORGANISM: Artificial Sequence
<220> FEATURE:
<223> OTHER INFORMATION: F5

<400> SEQUENCE: 31
agttacttcg attgatctca gct                                           23

<210> SEQ ID NO 32
<211> LENGTH: 22
<212> TYPE: DNA
<213> ORGANISM: Artificial Sequence
<220> FEATURE:
<223> OTHER INFORMATION: R5

<400> SEQUENCE: 32
gagagatcga gaccagtgag tg                                            22

<210> SEQ ID NO 33
<211> LENGTH: 20
<212> TYPE: DNA
<213> ORGANISM: Artificial Sequence
<220> FEATURE:
<223> OTHER INFORMATION: VTC2-2F

<400> SEQUENCE: 33
acgtccgaat cacaaccaca                                               20

<210> SEQ ID NO 34
<211> LENGTH: 23
<212> TYPE: DNA
<213> ORGANISM: Artificial Sequence
<220> FEATURE:
<223> OTHER INFORMATION: VTC2-2R

<400> SEQUENCE: 34
tgattagact cttccaagct aca                                           23

<210> SEQ ID NO 35
<211> LENGTH: 22
<212> TYPE: DNA
<213> ORGANISM: Artificial Sequence
<220> FEATURE:
<223> OTHER INFORMATION: VTC2-qPCR-F

<400> SEQUENCE: 35
ttcgctatga tgtcactgcc tg                                            22

<210> SEQ ID NO 36
<211> LENGTH: 21
<212> TYPE: DNA
<213> ORGANISM: Artificial Sequence
<220> FEATURE:

```
<223> OTHER INFORMATION: VTC2-qPCR-R

<400> SEQUENCE: 36
gcaacgaaac catacttccc c                                              21

<210> SEQ ID NO 37
<211> LENGTH: 21
<212> TYPE: DNA
<213> ORGANISM: Artificial Sequence
<220> FEATURE:
<223> OTHER INFORMATION: LsGGP1-F

<400> SEQUENCE: 37
tcgaattaat ttgcgactag c                                              21

<210> SEQ ID NO 38
<211> LENGTH: 22
<212> TYPE: DNA
<213> ORGANISM: Artificial Sequence
<220> FEATURE:
<223> OTHER INFORMATION: LsGGP1-R

<400> SEQUENCE: 38
cttcttcgat taattgggac gc                                             22

<210> SEQ ID NO 39
<211> LENGTH: 23
<212> TYPE: DNA
<213> ORGANISM: Artificial Sequence
<220> FEATURE:
<223> OTHER INFORMATION: LsGGP2-F

<400> SEQUENCE: 39
acactccaca cccatgaaat ctc                                            23

<210> SEQ ID NO 40
<211> LENGTH: 26
<212> TYPE: DNA
<213> ORGANISM: Artificial Sequence
<220> FEATURE:
<223> OTHER INFORMATION: LsGGP2-R

<400> SEQUENCE: 40
cttgaaaatt aaacgataat aacagg                                         26
```

METHOD FOR REGULATING GENE EXPRESSION

CROSS-REFERENCE TO RELATED APPLICATIONS

This application is a U.S. National Phase of International Patent Application No. PCT/CN2018/110928, filed on Oct. 19, 2018, which claims priority to Chinese Application No. 201710976945.0, filed Oct. 19, 2017. The entire contents of these applications are incorporated herein by reference in their entirety.

TECHNICAL FIELD

The invention relates to the field of genetic engineering. Specifically, it relates to a method of modifying an upstream open reading frame (uORF) by genome editing technique to regulate gene expression.

TECHNICAL BACKGROUND

Gene expression plays fundamental roles in determining the phenotypic diversity of living organisms. Artificial manipulation of gene expression is the key to optimizing the economic traits of industrial organisms, livestock animals and crop plants. Control of transcription is basic and common method of regulating gene expression, and translation of transcripts into protein can also be finely controlled by various means[1]. A leader sequence precedes the coding region in the mRNA of eukaryotes is referred to as the 5' untranslated region (5' UTR). Previous studies found that part of the 5' untranslated region contains an open reading frame (ORF) that may be translated, called the upstream open reading frame (uORF). There are increasing evidences showing that the presence of uORF is a crucial mechanism for regulating the translation of important protein-coding genes[2-5]. Genome-wide bioinformatic analysis has indicated that over 50% of human mRNAs and about 35% of *Arabidopsis thaliana* mRNAs contain at least one putative uORF. A number of studies have shown that uORFs frequently inhibit translation of the primary ORFs (pORFs). It has been reported that targeting uORFs with anti-sense oligonucleotides increased the translation efficiencies of pORFs[4]. However, the biological functions of the vast majority of the putative uORFs uncovered by bioinformatic investigations are still unknown. A recent study has shown that uORF can be employed to optimize the translation of plant immune genes so as to achieve a fine balance between disease resistance and cell growth processes. This study illustrates the pivotal effect of translation regulation on the function of critical genes and the potential power of utilizing uORFs for improving crop trait.

SUMMARY OF THE INVENTION

Translation regulation by upstream open reading frame (uORF) is emerging as a critical mechanism for controlling the function of many eukaryotic genes. The present inventors demonstrate that genome editing of uORFs is an efficient strategy for regulating the translation of genes in various organisms. The resulting mutants are useful for studying vital biological processes (e.g., AtBRI1 mediated brassinosteroid signaling) or improving valuable crop traits (e.g., ascorbic acid content).

DESCRIPTION OF THE DRAWINGS

FIG. 3. The 5'-leader sequence in the different genes used in the experiments. The uORFs are underlined. The putative initiation codons of uORFs are shaded, and the primary ORFs are labeled black. (a-d) The 5'-leader sequence of AtBRI1 (AT4G39400) (a), AtVTC2 (AT4G26850) (b), LsGGP1 (Lsat_1_v5_gn_7_113861)(c) and LsGGP2 (Lsat_1_v5_gn_5_3140)(d).

FIG. 5. Multiple alignment of putative AtVTC2, LsGGP1 and LsGGP2 proteins. Asterisk, colon and dot indicate identical, highly conserved and weakly conserved residues, respectively.

FIG. 8. Sequences of 35S promoter-fused wild type and mutated 5'-leader sequences of AtBRI1 and AtVTC2. In each synthesized fragment, the cleavage sites of restriction enzyme HindIII and NcoI are highlighted in green (bold) and orange (bold) respectively; the 35S promoter is shown in black, the uORF sequences in red, and the sequences surrounding the uORFs in blue.

FIG. 9. Genome editing of the uORF of CHLH to reduce the translation of CHLH. (a) Effects of WT and mutant uORFs of CHLH on LUC/REN activities as assessed using the dual luciferase reporter system. CHLH-C-Tm differed from CHLH-WT by the mutation of ACG to ATG, CHLH-C-Am differed from CHLH-WT by the mutation of GTG to ATG. The mean LUC/REN activity conferred by CHLH-C-Tm-LUC and CHLH-C-Am-LUC were normalized to those of CHLH-WT-LUC (n=3). (b) Effects of reduced CHLH expression on seedlings. (c) The 5'-leader sequence of CHLH. The potential uORFs are underlined. This 5'-leader sequence contains 2 potential uORFs, the first is ACG→ATG(CHLH-C-Tm), while the second GTG-ATG (CHLH-G-Am).

FIG. 11. Genome editing of the uORF of Cytochrome P450 to reduce the translation of Cytochrome P450. (a) Effects of WT and mutant uORFs of Cytochrome P450 on LUC/REN activities as assessed using the dual luciferase reporter system. CYTO-m differed from CYTO-WT by the mutation of ACG to ATG. The mean LUC/REN activity conferred by CYTO-m-LUC were normalized to those of CYTO-WT-LUC (n=3). (b) Effects of reduced Cytochrome P450 expression in response to herbicide (bensulfuron-methyl (BSM)). (c) The 5'-leader sequence of CYTO. The potential uORF is underlined. This 5'-leader sequence contains 1 potential uORF, ACG→ATG(CYTO-m).

FIG. 12. Genome editing of the uORF of SPINDLY to reduce the translation of SPINDLY. (a) Effects of WT and mutant uORFs of SPINDLY on LUC/REN activities as assessed using the dual luciferase reporter system. SPY-1C-Tm differed from SPY-WT by the mutation of ACG to ATG, SPY-2C-Tm differed from SPY-WT by the mutation of ACG to ATG. The mean LUC/REN activity conferred by SPY-1C-Tm-LUC and SPY-2C-Tm-LUC were normalized to those of SPY-WT-LUC (n=3). (b-c) Effects of reduced SPINDLY expression on growth of rice. (d) The 5'-leader sequence of SPINDLY. The potential uORFs are underlined. This 5'-leader sequence contains 2 potential uORFs, the first is ACG→ATG(SPY-1C-Tm), while the second ACG→ATG (SPY-2C-Tm).

FIG. 13. Genome editing of the uORF of PHOTOPERIOD SENSITIVITY 5 (SE5) to reduce the translation of SE5. (a) Effects of WT and mutant uORFs of PHOTOPERIOD SENSITIVITY 5 (SE5) on LUC/REN activities as assessed using the dual luciferase reporter system. SE5-1C-Tm differed from SE5-WT by the mutation of ACG to ATG SPY-2C-Tm differed from SE5-WT by the mutation of ACG to ATG. The mean LUC/REN activity conferred by SE5-1C-Tm-LUC and SE5-2C-Tm-LUC were normalized to those of SE5-WT-LUC (n=3). (b) Effects of reduced SE5 expression on flowering time in rice. (c) The 5'-leader sequence of SE5. The potential uORFs are underlined. This 5'-leader sequence contains 2 potential uORFs, the first is ACG→ATG(SE5-1C-Tm), while the second ACG-ATG (SE5-2C-Tm).

DETAILED DESCRIPTION OF THE INVENTION

1. Definition

Figure 1:
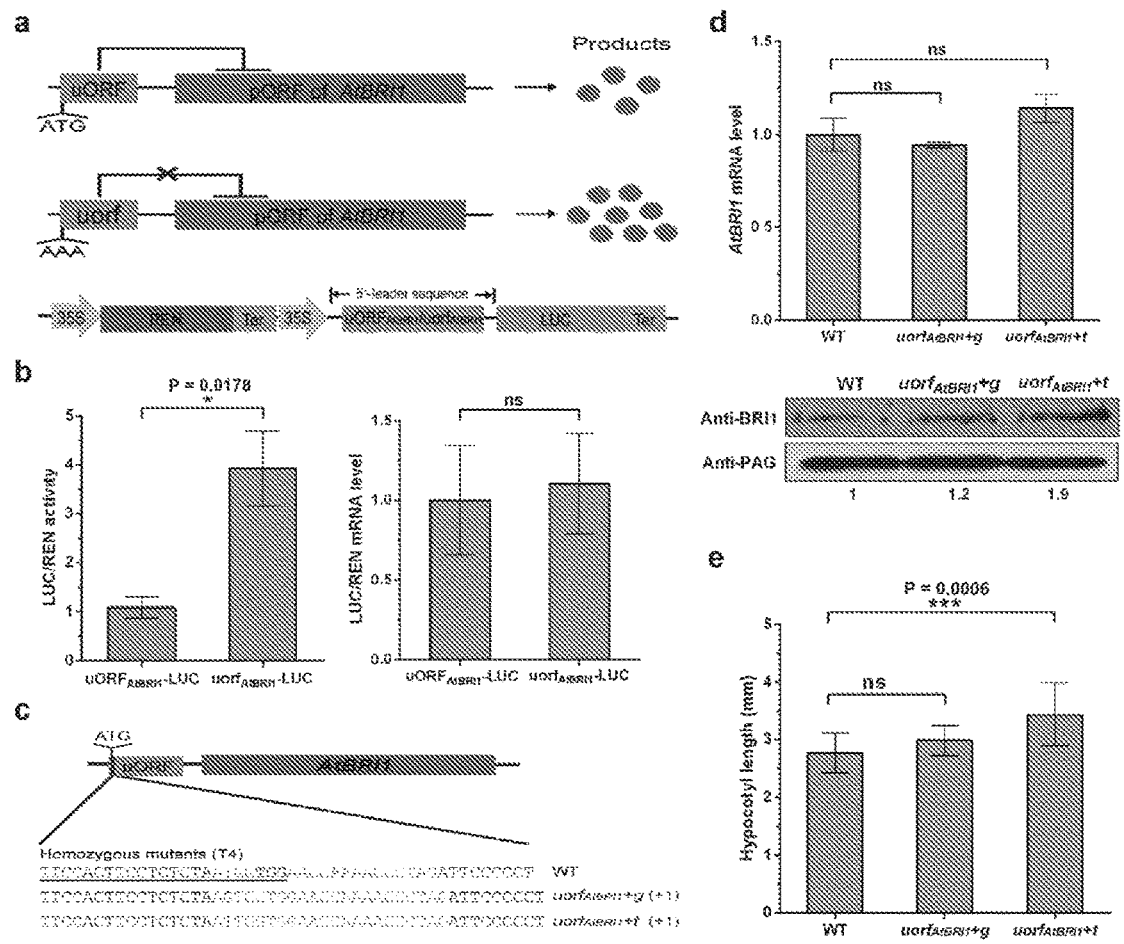
FIG. 1. CRISPR/Cas9 mediated editing of the uORF of AtBRI1 to enhance the translation of AtBRI1. (a) Schematic representation of WT uORF, mutant uorf and the dual-luciferase assay vector used to assess the effects of uORF on the translation of downstream AtBRI1 pORF. (b) Effects of WT and mutant forms of uORF on LUC/REN activity (left) and mRNA level (right) as analyzed with the dual luciferase system in *Arabidopsis* protoplasts incubated for 48 h. uORF$_{AtBRI1}$-LUC differed from uorf$_{AtBRI1}$-LUC by the mutation of uATG (in the former) to AAA (in the latter). The mean LUC/REN activity and mRNA levels conferred by uorf$_{ABRI1}$-LUC were normalized to those of uORF$_{AtBRI1}$-LUC (n=3). (c) CRISPR/Cas9-induced changes in the two homozygous mutants of the uORF of AtBRI1. Compared with WT control, the uATG in the two mutants (uorf$_{AtBRI1}$+g and uorf$_{AtBRI1}$+t) were disrupted by a single G or T insertion. The uORF sequence is in blue, and the sgRNA targeting sequence is underlined, with the proto-adjacent motif (PAM) shown in bold. (d) Comparison of AtBRI1 transcript (top panel) and protein (bottom panel) levels among WT control, uorf$_{AtBRI1}$+g and uorf$_{AtBRI1}$+t. *Arabidopsis* Actin2 (At3g18780) was used as internal control for the qRT-PCR assay (n=3). The 20S proteasome α-subunit G1 (PAG) was employed as loading control in Western blot analysis. The numbers below the blots show the relative amounts of AtBRI1 in the three genotypes, with the value of WT control arbitrarily set as 1. (e) Hypocotyl lengths of WT control, uorf$_{AtBRI1}$+g and uorf$_{AtBRI1}$+t seedlings grown in the presence of 2 µM brassinazole in the dark for 6 days (n=10). All values represent means±S.D. *P<0.05, ***P<0.001; ns, no significant difference by two-tailed Student's t-test.

In the present invention, the scientific and technical terms used herein have the meaning as commonly understood by a person skilled in the art unless otherwise specified. Also, the protein and nucleic acid chemistry, molecular biology, cell and tissue culture, microbiology, immunology related terms, and laboratory procedures used herein are terms and routine steps that are widely used in the corresponding field. For example, standard recombinant DNA and molecular cloning techniques used in the present invention are well known to those skilled in the art and are more fully described in the following document: Sambrook, J., Fritsch, E. F. and Maniatis, T., Molecular Cloning: A Laboratory Manual; Cold Spring Harbor Laboratory Press: Cold Spring Harbor, 1989 (hereinafter referred to as "Sambrook"). In the meantime, in order to better understand the present invention, definitions and explanations of related terms are provided below.

"Genome" as used herein encompasses not only chromosomal DNA present in the nucleus, but also organellar DNA present in the subcellular components (eg, mitochondria, plastids) of the cell.

As used herein, "organism" includes any organism that is suitable for genomic editing. Examples of organisms include, but are not limited to, mammals such as humans, mice, rats, monkeys, dogs, pigs, sheep, cattle, cats; poultry such as chickens, ducks, geese; plants including monocots and dicots such as rice, corn, wheat, sorghum, barley, soybean, peanut, *Arabidopsis* and the like.

"Exogenous" in reference to a sequence means a sequence from a foreign species, or refers to a sequence in which significant changes in composition and/or locus occur from its native form through deliberate human intervention if from the same species.

"Polynucleotide", "nucleic acid sequence", "nucleotide sequence" or "nucleic acid fragment" are used interchangeably and are single-stranded or double-stranded RNA or DNA polymers, optionally containing synthetic, non-natural or altered nucleotide bases. Nucleotides are referred to by their single letter names as follows: "A" is adenosine or deoxyadenosine (corresponding to RNA or DNA, respectively), "C" means cytidine or deoxycytidine, "G" means guanosine or deoxyguanosine, "U" represents uridine, "T" means deoxythymidine, "R" means purine (A or G), "Y" means pyrimidine (C or T), "K" means G or T, "H" means A or C or T, "I" means inosine, and "N" means any nucleotide.

"Polypeptide," "peptide," and "protein" are used interchangeably in the present invention to refer to a polymer of amino acid residues. The terms apply to an amino acid polymer in which one or more amino acid residues is artificial chemical analogue of corresponding naturally occurring amino acid(s), as well as to a naturally occurring amino acid polymer. The terms "polypeptide," "peptide," "amino acid sequence," and "protein" may also include modified forms including, but not limited to, glycosylation, lipid ligation, sulfation, y carboxylation of glutamic acid residues, and ADP-ribosylation.

As used in the present invention, "expression construct" refers to a vector such as a recombinant vector that is suitable for expression of a nucleotide sequence of interest in an organism. "Expression" refers to the production of a functional product. For example, expression of a nucleotide sequence may refer to the transcription of a nucleotide sequence (eg, transcription to produce mRNA or functional RNA) and/or the translation of an RNA into a precursor or mature protein.

The "expression construct" of the present invention may be a linear nucleic acid fragment, a circular plasmid, a viral vector or, in some embodiments, an RNA that is capable of translation (such as mRNA).

The "expression construct" of the present invention may comprise regulatory sequences and nucleotide sequences of interest from different origins, or regulatory sequences and nucleotide sequences of interest from the same source but arranged in a manner different from that normally occurring in nature.

"Regulatory sequence" and "regulatory element" are used interchangeably to refer to a nucleotide sequence that is located upstream (5' non-coding sequence), middle or downstream (3' non-coding sequence) of a coding sequence and affects the transcription, RNA processing or stability or translation of the relevant coding sequence.

Regulatory sequences may include, but are not limited to, promoters, translation leaders, introns and polyadenylation recognition sequences.

"Promoter" refers to a nucleic acid fragment capable of controlling the transcription of another nucleic acid fragment. In some embodiments of the present invention, the promoter is a promoter capable of controlling the transcription of a gene in a cell, whether or not it is derived from the cell. The promoter may be a constitutive promoter or tissue-specific promoter or developmentally-regulated promoter or inducible promoter.

"Constitutive promoter" refers to a promoter that may in general cause the gene to be expressed in most cases in most cell types. "Tissue-specific promoter" and "tissue-preferred promoter" are used interchangeably and mean that they are expressed primarily but not necessarily exclusively in one tissue or organ, but also in a specific cell or cell type. "Developmentally-regulated promoter" refers to a promoter whose activity is dictated by developmental events. "Inducible promoter" selectively express operably linked DNA sequences in response to an endogenous or exogenous stimulus (environment, hormones, chemical signals, etc.).

Examples of promoters that can be used in the present invention include, but are not limited to, the polymerase (pol) I, pol II or pol III promoters. Examples of the pol I promoter include the gallus RNA pol I promoter. Examples of the pol II promoters include, but are not limited to, the immediate-early cytomegalovirus (CMV) promoter, the Rous sarcoma virus long terminal repeat (RSV-LTR) promoter, and the immediate-early simian virus 40 (SV40) promoter. Examples of pol III promoters include the U6 and H1 promoters. An inducible promoter such as a metallothionein promoter can be used. Other examples of promoters include the T7 phage promoter, the T3 phage promoter, the β-galactosidase promoter, and the Sp6 phage promoter, and the like. Promoters that can be used in plants include, but are not limited to, cauliflower mosaic virus 35S promoter, maize Ubi-1 promoter, wheat U6 promoter, rice U3 promoter, and rice actin promoter, and the like.

As used herein, the term "operably linked" refers to the linkage of a regulatory element (eg, but not limited to, a promoter sequence, a transcription termination sequence, etc.) to a nucleic acid sequence (eg, a coding sequence or an open reading frame) such that transcription of the nucleotide sequence is controlled and regulated by the transcriptional regulatory element. Techniques for operably linking regulatory element regions to nucleic acid molecules are known in the art.

"Introduction" of a nucleic acid molecule (eg, plasmid, linear nucleic acid fragment, RNA, etc.) or protein into an organism means that the nucleic acid or protein is used to transform an organism cell such that the nucleic acid or protein is capable of functioning in the cell. As used in the present invention, "transformation" includes both stable and transient transformations. "Stable transformation" refers to the introduction of exogenous nucleotide sequences into the genome, resulting in the stable inheritance of foreign genes. Once stably transformed, the exogenous nucleic acid sequence is stably integrated into the genome of the organism and any of its successive generations. "Transient transformation" refers to the introduction of a nucleic acid molecule or protein into a cell, performing a function without the stable inheritance of an exogenous gene. In transient transformation, the exogenous nucleic acid sequences are not integrated into the genome. Methods that can be used to introduce nucleic acid molecules or proteins into an organism or a cell include, but are not limited to, calcium phosphate transfection, protoplast fusion, electroporation, lipofection, microinjection, viral infection (eg, baculovirus, vaccinia virus, Adenovirus and other viruses), gene gun method, PEG-mediated protoplast transformation, *Agrobacterium*-mediated transformation.

As used herein, the term "plant" includes a whole plant and any descendant, cell, tissue, or part of a plant. The term "plant parts" include any part(s) of a plant, including, for example and without limitation: seed (including mature seed and immature seed); a plant cutting; a plant cell; a plant cell culture; a plant organ (e.g., pollen, embryos, flowers, fruits, shoots, leaves, roots, stems, and explants). A plant tissue or plant organ may be a seed, protoplast, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. In contrast, some plant cells are not capable of being regenerated to produce plants. Regenerable cells in a plant cell or tissue culture may be embryos, protoplasts, meristematic cells, callus, pollen, leaves, anthers, roots, root tips, silk, flowers, kernels, ears, cobs, husks, or stalks.

Plant parts include harvestable parts and parts useful for propagation of progeny plants. Plant parts useful for propagation include, for example and without limitation: seed; fruit; a cutting; a seedling; a tuber; and a rootstock. A harvestable part of a plant may be any useful part of a plant, including, for example and without limitation: flower; pollen; seedling; tuber; leaf; stem; fruit; seed; and root.

A plant cell is the structural and physiological unit of the plant, and includes protoplast cells without a cell wall and plant cells with a cell wall. A plant cell may be in the form of an isolated single cell, or an aggregate of cells (e.g., a friable callus and a cultured cell), and may be part of a higher organized unit (e.g., a plant tissue, plant organ, and plant). Thus, a plant cell may be a protoplast, a gamete producing cell, or a cell or collection of cells that can regenerate into a whole plant. As such, a seed, which comprises multiple plant cells and is capable of regenerating into a whole plant, is considered a "plant cell" in embodiments herein.

The term "protoplast", as used herein, refers to a plant cell that had its cell wall completely or partially removed, with the lipid bilayer membrane thereof naked, and thus includes protoplasts, which have their cell wall entirely removed, and spheroplasts, which have their cell wall only partially removed, but is not limited thereto. Typically, a protoplast is an isolated plant cell without cell walls which has the potency for regeneration into cell culture or a whole plant.

"Progeny" of a plant comprises any subsequent generation of the plant.

A "genetically modified plant" includes a plant which comprises within its genome an exogenous polynucleotide. For example, the exogenous polynucleotide is stably integrated within the genome such that the polynucleotide is passed on to successive generations. The exogenous polynucleotide may be integrated into the genome alone or as part of a recombinant DNA construct. The modified gene or expression regulatory sequence means that, in the plant genome, said sequence comprises one or more nucleotide substitution, deletion, or addition.

"Trait" refers to the physiological, morphological, biochemical, or physical characteristics of a plant or a particular plant material or cell. In some embodiments, the characteristic is visible to the human eye, such as seed or plant size, or can be measured by biochemical techniques, such as detecting the protein, starch, or oil content of seed or leaves, or by observation of a metabolic or physiological process, e.g. by measuring tolerance to water deprivation or particular salt or sugar concentrations, or by the observation of the expression level of a gene or genes, or by agricultural observations such as osmotic stress tolerance or yield. In some embodiments, trait also includes ploidy of a plant, such as haploidy which is important for plant breeding. In some embodiments, trait also includes resistance of a plant to herbicides.

"Agronomic trait" is a measurable parameter including but not limited to, leaf greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, harvest index, stalk lodging, plant height, ear height, ear length, disease resistance, cold resistance, salt tolerance, and tiller number and so on.

2. Regulating Gene Expression by Genome Editing of uORF

In one aspect, the present invention provides a method of regulating expression of a target protein in a cell, wherein the 5' untranslated region (5'-UTR) of the encoding gene of the target protein comprises an upstream open reading frame (uORF), wherein the method comprises introducing into the cell a genome editing system that targets the uORF, thereby increasing or decreasing or eliminating inhibition of target protein expression by the uORF.

In some embodiments, the introduction of the genome editing system that targets the uORF results in mutation of one or more nucleotides in the uORF, such as substitution, deletion or addition of one or more nucleotides.

In some embodiments, the mutation of one or more nucleotides results in a weak translation initiation codon of the uORF being mutated into a strong translation initiation codon, or the mutation results in a strong translation initiation codon of the uORF being mutated into a weak translation initiation codon, or the mutation results in the uORF not being translated. The strong translation initiation codon is, for example, ATG; the weak translation initiation codon is, for example, GTG, ATC, ACG TTG or AAG. In general, mutation of the uORF from a weak translation initiation codon to a strong translation initiation codon will likely enhance the inhibition of target protein expression by the uORF, thereby reducing target protein expression levels; uORF mutation from strong translation initiation codons to weak translation initiation codon will likely reduce the inhibition of the target protein expression by the uORF, thereby increasing the expression level of the target protein; and if the uORF is not translated, it may eliminate its inhibition of target protein expression, thereby increasing the expression level of the target protein. In addition, translation initiation codons such as ATG GTG ATC, ACG TTG or AAG have varying degrees of translation initiation capability, thereby enabling different levels of target protein expression regulation.

In another aspect, the present invention provides a method of regulating expression of a target protein in a cell, comprising introducing into said cell a genome editing system that targets the 5' untranslated region (5'-UTR) of the encoding gene of said target protein, thereby resulting in a mutation of one or more nucleotides in the 5'-UTR, the mutation results in the formation of an upstream open reading frame (uORF) in the 5'-UTR that inhibits expression of the target protein. For example, by replacing the C in the 5'-UTR of the gene with T by the single base editing, an additional ATG at the upstream of the main open reading frame can be artificially generated to form an artificial uORF, thereby regulating expression of the target protein.

The present invention does not particularly limit the genome editing system as used as long as it enables accurate editing of the genome of an organism or a cell. For example, genome editing systems suitable for use with the present invention include, but are not limited to, precise base editing (PBE) systems, CRISPR-Cas9 systems, CRISPR-Cpf1 systems, CRISPRi systems, zinc finger nuclease systems, and TALEN systems. Those skilled in the art will be able to select or design a suitable genome editing system in accordance with the teachings of the present invention.

CRISPR systems are produced by bacteria during evolution to protect against foreign gene invasion. It has been modified and widely used in genome editing of eukaryotes.

CRISPR-Cas9 system refers to a Cas9 nuclease-based genome CRISPR editing system. "Cas9 nuclease" and "Cas9" are used interchangeably herein and refer to an RNA Guided nuclease that include a Cas9 protein or fragment thereof (eg, a protein comprising the active DNA cleavage domain of Cas9 and/or the gRNA binding domain of Cas9). Cas9 is a component of the prokaryotic immune system of CRISPR/Cas that can target and cleave DNA target sequences to form DNA double-strand breaks (DSBs) under the guidance of guide RNA. CRISPR-Cas9 systems suitable for use in the present invention include, but are not limited to, those described in Shan, Q. et al. Targeted genome modification of crop plants using a CRISPR-Cas system. Nat. Biotechnol. 31, 686-688 (2013).

"guide RNA" and "gRNA" can be used interchangeably herein, which typically are composed of crRNA and tracrRNA molecules forming complexes through partial complement, wherein crRNA comprises a sequence that is sufficiently complementary to a target sequence for hybridization and directs the CRISPR complex (Cas9+crRNA+tracrRNA) to specifically bind to the target sequence. However, it is known in the art that single guide RNA (sgRNA) can be designed, which comprises the characteristics of both crRNA and tracrRNA.

The CRISPR-Cas9 system of the present invention may include one of the following:
i) a Cas9 protein, and a guide RNA;
ii) an expression construct comprising a nucleotide sequence encoding a Cas9 protein, and a guide RNA;
iii) a Cas9 protein, and an expression construct comprising a nucleotide sequence encoding a guide RNA;
iv) an expression construct comprising a nucleotide sequence encoding a Cas9 protein, and an expression construct comprising a nucleotide sequence encoding a guide RNA; or
v) an expression construct comprising a nucleotide sequence encoding a Cas9 protein and a nucleotide sequence encoding a guide RNA.

The CRISPR-Cpf1 system is a CRISPR genome editing system based on the Cpf1 nuclease. The difference between Cpf1 and Cas9 is that the molecular weight of the Cpf1 protein is small, and only crRNA is required as the guide RNA, and the PAM sequence is also different. The CRISPR-Cpf1 system suitable for use in the present invention includes, but is not limited to, the system described in Tang et al., 2017.

The CRISPR-Cpf1 system of the present invention may include one of the following:
i) a Cpf1 protein, and a guide RNA (crRNA);
ii) an expression construct comprising a nucleotide sequence encoding a Cpf1 protein, and a guide RNA;
iii) a Cpf1 protein, and an expression construct comprising a nucleotide sequence encoding a guide RNA;
iv) an expression construct comprising a nucleotide sequence encoding a Cpf1 protein, and an expression construct comprising a nucleotide sequence encoding a guide RNA; or
v) an expression construct comprising a nucleotide sequence encoding a Cpf1 protein and a nucleotide sequence encoding a guide RNA.

CRISPR interference (CRISPRi) is a gene silencing system derived from the CRISPR-Cas9 system that uses a nuclease-inactivated Cas9 protein. Although this system does not change the sequence of the target gene, it is also defined herein as a genome editing system. CRISPRi systems suitable for use with the present invention include, but are not limited to, the system described in Seth and Harish, 2016.

The CRISPRi system of the present invention may include one of the following:
i) a nuclease-inactivated Cas9 protein, and a guide RNA;
ii) an expression construct comprising a nucleotide sequence encoding a nuclease-inactivated Cas9 protein, and a guide RNA;
iii) a nuclease-inactivated Cas9 protein, and an expression construct comprising a nucleotide sequence encoding a guide RNA;
iv) an expression construct comprising a nucleotide sequence encoding a nuclease-inactivated Cas9 protein, and an expression construct comprising a nucleotide sequence encoding a guide RNA; or
v) an expression construct comprising a nucleotide sequence encoding a nuclease-inactivated Cas9 protein and a nucleotide sequence encoding a guide RNA.

The precise base editor system is a system that has recently been developed based on CRISPR-Cas9, which enables accurate single-base editing of a genome using a nuclease-inactivated fusion protein of Cas9 protein and cytidine deaminase. Nuclease-inactivated Cas9 (due to mutations in the HNH subdomain and/or RuvC subdomain of the DNA cleavage domain) retains gRNA-directed DNA-binding ability, and the cytidine deaminase can catalyze deamination of cytidine (C) on DNA to form uracil (U). The nuclease-inactivated Cas9 is fused with a cytidine deaminase. Under the guidance of the guide RNA, the fusion protein can target the target sequence in the plant genome. Due to the absence of the Cas9 nuclease activity, the DNA double strand is not cleaved. The deaminase domain in the fusion protein converts the cytidine of the single-stranded DNA produced in the formation of the Cas9-gRNA-DNA complex to U, and the substitution of C to T is achieved by base mismatch repair. The precise base editor system suitable for use in the present invention includes, but is not limited to, the system described in Zong et al., 2017.

The precise base editor system of the present invention may include one of the following:
i) a fusion protein of nuclease-inactivated Cas9 and cytidine deaminase, and guide RNA;
ii) an expression construct comprising the nucleotide sequence encoding a fusion protein of a nuclease-inactivated Cas9 protein and a cytidine deaminase, and a guide RNA;
iii) a fusion protein of nuclease-inactivated Cas9 protein and cytidine deaminase, and an expression construct comprising a nucleotide sequence encoding a guide RNA;
iv) an expression construct comprising a nucleotide sequence encoding a fusion protein of a nuclease-inactivated Cas9 protein and a cytidine deaminase, and an expression construct comprising a nucleotide sequence encoding a guide RNA; or
v) an expression construct comprising a nucleotide sequence encoding a fusion protein of a nuclease-inactivated Cas9 protein and a cytidine deaminase and a nucleotide sequence encoding a guide RNA.

In some embodiments, the nuclease-inactivated Cas9 protein comprises amino acid substitutions D10A and/or H840A relative to wild-type Cas9 (S. pyogenes SpCas9). Examples of the cytidine deaminase include, but are not limited to, APOBEC1 deaminase, activation-induced cytidine deaminase (AID), APOBEC3G, or CDA1(PmCDA1).

"Zinc finger nuclease (ZFN)" is an artificial restriction enzyme prepared by fusing a zinc finger DNA binding domain with a DNA cleavage domain. The zinc finger DNA binding domain of a single ZFN typically contains 3-6 individual zinc finger repeats, each zinc finger repeat recognizing, for example, 3 bp. ZFN systems suitable for use in the present invention can be obtained, for example, from Shukla et al., 2009 and Townsend et al., 2009.

"Transactivator-like effector nucleases (TALENs)" are restriction enzymes that can be engineered to cleave specific DNA sequences, usually prepared by fusion of the DNA binding domain of the transcriptional activator-like effector (TALE) and a DNA cleavage domain. TALE can be engineered to bind almost any desired DNA sequences. The TALEN system suitable for use in the present invention can be obtained, for example, from Li et al., 2012.

In some embodiments of the methods of the present invention, the cell is a cell of mammals such as human, mouse, rat, monkey, dog, pig, sheep, cattle, cat; a cell of poultry such as chicken, duck, goose; a cell of plants including monocots and dicots, particularly crop plants such as rice, corn, wheat, sorghum, barley, soybean, and peanut, or model plants such as Arabidopsis thaliana, or vegetable plants such as Lactuca sativa.

In another aspect, the present invention provides a cell modified by the method of the present invention, wherein the expression level of the target protein in the cell is altered relative to an unmodified cell.

In some embodiments, the cell is a plant cell.

In another aspect, the invention provides a method of producing a genetically modified plant, comprising the step of regenerating an intact plant from the modified plant cell of the invention, wherein the expression level of the target protein in the genetically modified plant is altered relative to a plant that has not been genetically modified. In some embodiments, a change in the expression level of the target protein results in a change in the plant trait, preferably an agronomic trait. Such plants include, but are not limited to, monocots or dicots, particularly crop plants such as rice, corn, wheat, sorghum, barley, soybean, and peanut, or model plants such as Arabidopsis thaliana, or vegetable plants such as Lactuca sativa.

In some embodiments, the target protein in the plant is BRI1. In some embodiments, the encoding gene of the BRI1 protein is AtBRI1 (Arabidopsis thaliana). Alterations in BRI1 expression may alter the brassinosteroid signal transduction in the plant, thereby altering the associated traits.

In some embodiments, the target protein in the plant is GDP-L-galactose phosphorylase (GGP). In some embodiments, the encoding gene of the GDP-L-galactose phosphorylase are AtVTC2 (Arabidopsis thaliana), LsGGP1(Lactuca sativa), and LsGGP2 (Lactuca sativa). The level of ascorbic acid in genetically modified plants with altered GGP expression will be altered relative to the wild type control, preferably, with increasing levels of ascorbic acid relative to the wild type control.

In some embodiments, the genetically modified plant of the invention is transgene-free. For example, genetically modified transgene-free plants can be obtained by transient transformation of the genome editing system. Alternatively, genetically modified transgene-free plants can be obtained by genetic segregation in the progeny after obtaining a genetically modified plant with integrated exogenous transgene.

In some embodiments, the encoding gene of the target protein in the plant is CHLH, such as rice CHLH gene. Alterations in CHLH expression may effect chlorophyll synthesis, when T-DNA simultaneously (homozygous) disrupts the function of the gene, causing albino seedlings.

In some embodiments, the encoding gene of the target protein in the plant is Eukaryotic initiation factor iso-4F gene. Alterations in Eukaryotic initiation factor iso-4F expression may provide resistance to specific virus.

In some embodiments, the encoding gene of the target protein in the plant is Cytochrome P450 gene. Alterations in Cytochrome P450 expression may make seedlings more sensitive to herbicides (bensulfuron-methyl (BSM)), thus showing slow growth.

In some embodiments, the encoding gene of the target protein in the plant is SPINDLY gene, such as rice SPINDLY gene. Alterations in SPINDLY expression may increase internode growth during vegetative growth.

In some embodiments, the encoding gene of the target protein in the plant is PHOTOPERIOD SENSITIVITY 5 (SE5), such as rice SE5 gene. Alterations in SE5 expression may show early flowering under long-day conditions.

In another aspect, the present invention encompasses genetically modified plants produced by the methods of the present invention or progeny thereof.

EXAMPLES

Further understanding to the present invention can be obtained with reference to specific examples provided herein. These examples are only illustrative of the invention, and it is not intended to make any limitation as to the scope of the invention. It is apparent that various modifications and changes can be made to the present invention without departing from the spirit of the invention, and such modifications and variations are also within the scope of the present invention.

Material and Method

Plasmid Construction

To generate mutants of uORFs in AtBRI1 and AtVTC2, pYAO:hSpCas9-AtBRI1uORF-sgRNA and pYAO:hSpCas9-AtVTC2uORF-sgRNA were prepared as previously reported[17]. Briefly, AtU6-26-AtBRI1uORF-sgRNA and AtU6-26-AtVTC2uORF-sgRNA were constructed with the primers listed in Table 1 and the BsaI-digested AtU6-26-SK (origin), then were digested using SpeI and NheI, and cloned into SpeI digested pYAO:hspCas9.

To produce uORF mutants for LsGGP1 and LsGGP2, pKSE401-LGGP1uORF-sgRNA and pKSE401-LsGGP2uORF-sgRNA were constructed as previously described[18]. The BsaI-digested pKSE401 was used to insert the sgRNAs, which were prepared with the primers listed in Table 1.

For developing the constructs used in the dual luciferase assay, the 35S promoter-fused WT and mutated forms of 5'-leader sequences of each gene (FIG. 8) were synthesized commercially (Generaybio, Beijing, China). They were then cloned into the pGreenII0800-LUC[19] vector digested with HindIII and NcoI. The correctness of the cloning was verified by DNA sequencing.

TABLE 1

Target sites of two genes in Arabidopsis and two genes in lettuce, and oligo sequences for constructing sgRNAs.

| Target gene | Target sequence (PAM is underlined) (5'-3') | Oligo-F (5'-3') | Oligo-R (5'-3') |
| --- | --- | --- | --- |
| AtBRI1 | TTCCACTTCCTCTCTAATGGTGG | ATTGTTCCACTTCCTCTCTAATGG | AAACCCATTAGAGAGGAAGTGGAA |
| AtVTC2 | GGAACAGGTGATCGGAATCACGG | ATTGGGAACAGGTGATCGGAATCA | AAACTGATTCCGATCACCTGTTCC |
| LsGGP1 | CCACGGCTATACACGGAGCACA | ATTGTGTGCTCCGTGTATAGCCG | AAACCGGCTATACACGGAGCACA |
| LsGGP2 | CGACAAGTTGCAGACATCACGG | ATTGCGACAAGTTGCAGACATCA | AAACTGATGTCTGCAACTTGTCG |

Generation of uORF Mutants for AtBRI1 and AtVTC2

The uORF mutants of AtBRI1 and AtVTC2 were generated by genetic transformation of Arabidopsis (ecotype Col-0) using flower dipping with the vectors pYAO:hSpCas9-AtBRI1uORF-sgRNA and pYAO:hSpCas9-AtVTC2uORF-sgRNA, respectively. The resulting mutants were verified by sequencing the PCR products amplified with targeting site-specific primers (Table 2). Transgene-free mutants were selected by PCR using four pairs of primers (Table 2), and verified by their lack of antibiotic resistance.

Arabidopsis Growth and Protoplast Transfection

Arabidopsis protoplasts were isolated from 14-d old seedlings grown on ½ MS medium[20]. They were transfected by pGreenII0800-p35S:AtBRI1-5'-leader-LUC, pGreenII0800-p35S:AtVTC2-5'-leader-LUC or the constructs carrying the mutated forms of the relevant 5'-leader sequences following a previously reported protocol[21]. In each transfection, 20 μg plasmid DNA and approximately $5 \times 10^5$ protoplasts were used. Two days after transfection, the protoplasts were harvested by centrifugation at 100 g for 5 min. LUC/REN

TABLE 2

Primers used

| Primer name | Primer sequence (5'-3') | Application |
| --- | --- | --- |
| qPCR-LUC-F | GGATTACAAGATTCAAAGTGCG | qPCR for LUC expression level |
| qPCR-LUC-R | TGATACCTGGCAGATGGAAC | |
| qPCR-REN-F | CATGGGATGAATGGCCTGATATTG | qPCR for REN expression level |
| qPCR-REN-R | GATAATGTTGGACGACGAACTTC | |
| BRI1-F1 | AAGTAGGATATGTAGCTTGCAGAAG | Amplifying the AtBRI1 target site |
| BRI1-R1 | AGATCCAGAACTTCCAAGCTG | |
| BRI1-RNA-F | TTGGTTCTTGCTCCGGTCTG | qPCR for AtBRI1 expression level |
| BRI1-RNA-R | CGTCTCCACTGATTTTGTTTCC | |
| Actin2-F | GCACCCTGTTCTTCTTACCG | qPCR for AtActin2 expression level |
| Actin2-R | AACCCTCGTAGATTGGCACA | |
| F1 | CCAGTCACGACGTTGTAAAAC | Detecting CRISPR/Cas9 construct |
| R1 | CAATGAATTTCCCATCGTCGAG | |
| F2 | CTCGAGGAAGCTTCTAGATTTC | Detecting CRISPR/Cas9 construct |
| R2 | GATCCTTGTAGTCTCCGTCGTGG | |
| F3 | CATCCAGAAAGCCCAGGTGTC | Detecting CRISPR/Cas9 construct |
| R3 | CAGGGTAATCTCGGTCTTG | |
| F4 | CATCATGGAAAGAAGCAGCTT | Detecting CRISPR/Cas9 construct |
| R4 | GAATTCCCGATCTAGTAACATAGA | |
| F5 | AGTTACTTCGATTGATCTCAGCT | Amplifying the fragment of AtBRI1 |
| R5 | GAGAGATCGAGACCAGTGAGTG | |
| VTC2-2F | ACGTCCGAATCACAACCACA | Amplifying the AtVTC2 target site |
| VTC2-2R | TGATTAGACTCTTCCAAGCTACA | |
| VTC2-qPCR-F | TTCGCTATGATGTCACTGCCTG | qPCR for AtVTC2 expression level |
| VTC2-qPCR-R | GCAACGAAACCATACTTCCCC | |
| LsGGP1-F | TCGAATTAATTTGCGACTAGC | Amplifying the LsGGP1 target site |
| LsGGP1-R | CTTCTTCGATTAATTGGGACGC | |
| LsGGP2-F | ACACTCCACACCCATGAAATCTC | Amplifying the LsGGP2 target site |
| LsGGP2-R | CTTGAAAATTAAACGATAATAACAGG | | activity was measured with the Dual-Luciferase® Reporter Assay System (Promega, Madison, USA). The LUC/REN levels conferred by the constructs with mutated 5'-leader sequences were calculated relative to those produced by pGreenII0800-p35S:AtBRI1-5'-leader-LUC or pGreenII0800-p35S:AtVTC2-5'-leader-LUC.

RNA Preparation and qRT-PCR

Total RNA was extracted from the desired protoplasts and plant samples with the eZNA™ plant RNA kit (Omega bio-tek, Norcross, USA). Reverse transcription was performed using M-MLV Reverse Transcriptase (Promega, Madison, USA). Subsequently, qRT-PCR was performed using SsoFast EvaGreen Supermix kit (Bio-Rad, Hercules, USA) following supplier's instruction. The primers used are listed in Table 2.

Agrobacterium-Mediated Lettuce Transformation and Preparation of uORF Mutants for LsGGP1 and LsGGP2

Iceberg lettuce (*Lactuca sativa* L. var. *capitata*) seeds were surface-sterilized with 70% ethanol for 1 min, followed by submersion in 1.0% sodium hypochlorite solution for 15 min, and then sown on the MS medium solidified with 0.8% Bacto agar (BD, Sparks, USA) and supplemented with 3% sucrose. The plates were incubated under a photoperiod of 16 h light (150 µmol m$^{-2}$ s$^{-1}$) and 8 h dark at 25° C. for 7 days. The cotyledon explants were aseptically excised from germinated seedlings and placed upside down on the MS co-cultivation medium (supplemented with 30 g/l sucrose, 0.8% plant agar, 0.1 mg/l α-naphthalaneacetic acid, and 0.5 mg/l 6-benzylaminopurine) for two days. Then the explants were incubated for 10 min with the *Agrobacterium* suspension carrying the desired construct (pKSE401-LsGGP1uORF-sgRNA, pKSE401-LsGGP2uORF-sgRNA or the empty vector pKSE401). Following co-cultivation, the excess *Agrobacterium* cells in the explants were removed with sterile filter paper. The treated explants were placed upside down on the MS co-cultivation medium again and incubated at 25° C. in dark for 48 h. Afterwards, the explants were transferred to the MS selection medium (supplemented with 30 g/l sucrose, 0.8% plant agar, 0.1 mg/l α-naphthalaneacetic acid, 0.5 mg/l 6-benzylaminopurine, 40 mg/L kanamycin monosulfate, and 250 mg/L carbenicilin), and incubated under a 16 h light (150 µmol m$^2$ s) and 8 h dark cycle at 25° C. After 15 days, the calli (4-8 millimeters in diameter) were subcultured on fresh MS selection medium. Ten days later, the calli with regenerated shoots were transferred to the MS selection medium containing reduced amounts of α-naphthalaneacetic acid (0.026 mg/l) and 6-benzylaminopurine (0.046 mg/l). When the shoots reached 3 cm, they were transferred to the MS rooting medium (½ MS supplemented with 15 g/l sucrose, 0.1 mg/l 3-indole acetic acid, and 250 mg/L carbenicilin) for root induction. The plantlets with well-developed shoot and root were each examined for uORF mutations as described above.

Protein Extraction and Protein Gel Blot Analysis

Protein was extracted from 14-d old *Arabidopsis* seedlings with an extraction buffer containing 50 mM Tris-HCl pH 7.5, 150 mM NaCl, 0.1% NP40, 4 M urea, and 1 mM PMSF. Protein gel blot analysis was performed with an anti-AtBRI1 antibody[22] (1:1500 dilution) or an anti-PAG1 antibody[23] (1:10,000 dilution). The secondary antibody employed was a goat anti-rabbit antibody conjugated to horseradish peroxidase, with the reaction signals visualized using an enhanced chemiluminescence solution (Millipore, Billerica, USA).

Determination of AsA Content

AsA content was determined by high-performance liquid chromatography (HPLC) following a previously detailed protocol[24]. In brief, leaf tissues were ground to powder in liquid nitrogen. The powder was solubilized using an extraction buffer, which contained 74.45 mg EDTA, 286.65 mg TCEP and 5 ml of 98% orthophosphoric acid in a final volume of 100 ml Milli-Q water. The suspension was vortexed for 30 sec, followed by an incubation at room temperature for 2 min and then on ice for 10 min. Subsequently, they were centrifuged at 12,000 g at 4° C. for 30 min, with the supernatant retained and filtered using 4 mm hydrophilic PTFE syringe filter. The filtrated samples were assayed using Pursuit XRs C18 A2000250X046 column (Agilent), and detected by ultraviolet (244 nm). For the homozygous uORF mutants of AtVTC2, three biological replicates, each containing the foliar tissues from 6 seedlings, were assayed. For the T0 uORF mutants of LsGGP1 or LsGGP2, the seedlings with mutant allele(s) were individually assayed for AsA content using the foliar tissues. The plantlets with the empty T-DNA of pKSE401 were used as controls during AsA measurement.

Statistical Analysis

All numerical values were presented as means±S.D. Statistical differences in between different samples were tested using two-tailed Student's t-test.

Example 1 Determining uORF$_{AtBRI1}$ by Dual-Luciferase Reporter Assay

Figure 3:
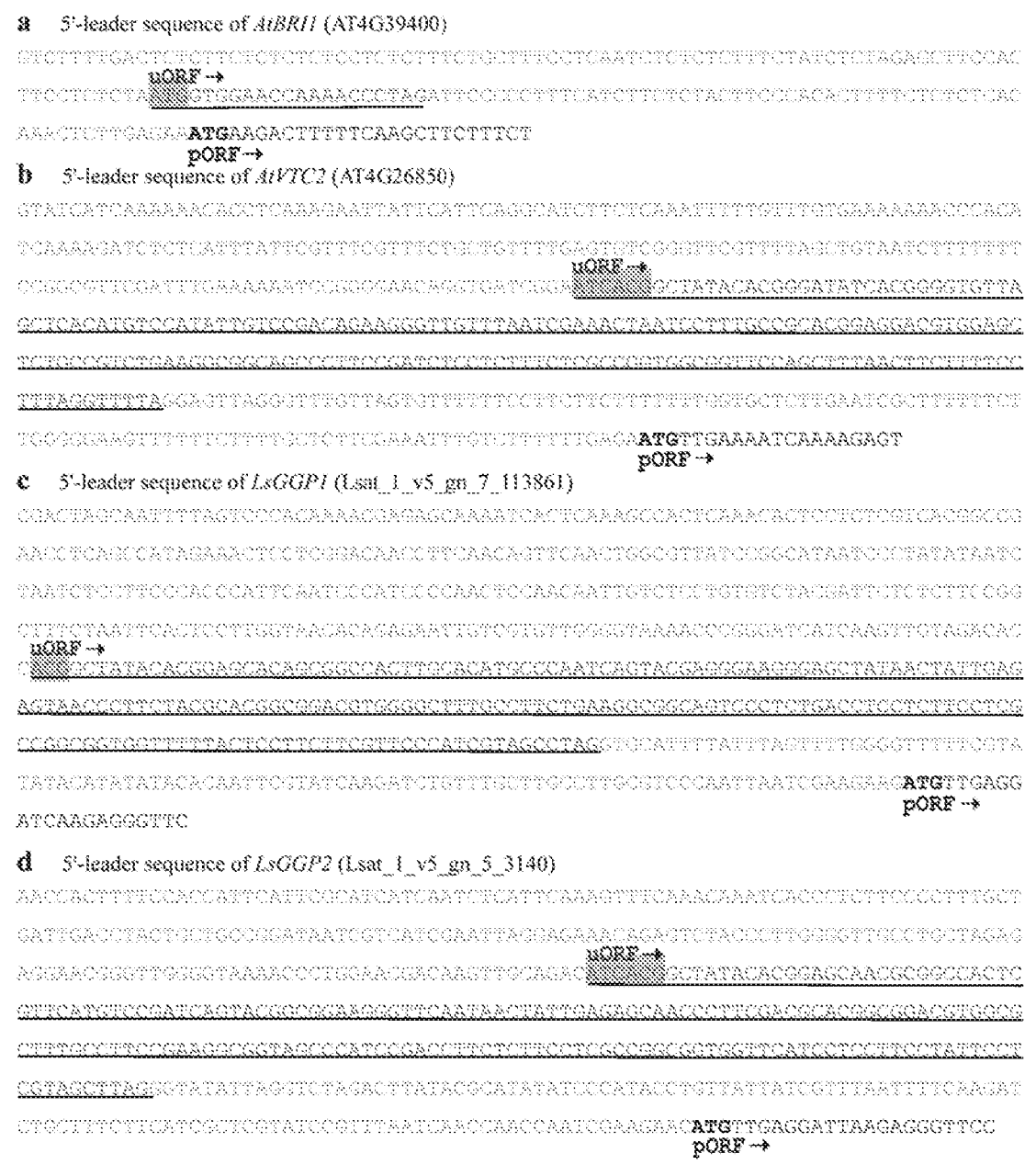

As a proof of concept, the inventors analyzed a putative uORF located in the 5'-leader sequence of AtBRI1, whose product is a receptor for the phytohormone brassinosteroid (BR) in *Arabidopsis*[6]. The uORF (designated uORF$_{AtBRI1}$) starts with ATG, and is 21 bp long and located 58 bp upstream of the pORF encoding AtBRI1 (FIG. 1*a* and FIG. 3*a*).

To test if this putative uORF affects pORF translation, a dual-luciferase reporter assay is employed (FIG. 1*a*)[7]. The 5'-leader sequence of AtBRI1 together with either wild type (WT) uORF$_{AtBRI1}$ or a mutant form of uORF$_{AtBRI1}$ (designated uorf$_{AtBRI1}$) [with the upstream ATG (uATG) mutated to AAA] was inserted upstream of the luciferase (LUC) coding region, and the resulting expression cassettes were driven by the 35S promoter. As an internal control, a 35S promoter-directed cassette expressing *Renilla reniformis* luciferase (REN) was constructed in the same plasmid (FIG. 1*a*). The constructs carrying either uORF$_{ABRI1}$ or uorf$_{AtBRI1}$ were transiently expressed in *Arabidopsis* protoplasts. The construct with uorf$_{AtBRI1}$ generated nearly four-fold higher LUC/REN activities than the construct with WT uORF$_{AtBRI1}$ (FIG. 1*b*, left panel), while the corresponding mRNA levels did not differ significantly (FIG. 1*b*, right panel). These results suggest that LUC translation is markedly inhibited by the presence of the WT form of uORF$_{AtBRI1}$, the mutation of which can substantially enhance the translation of downstream pORF.

Example 2 Editing uORF$_{AtBRI}$1

We next performed CRISPR editing with an sgRNA targeting the region harboring the uATG (FIG. 1*c*) in order to assess the in vivo effects of disrupting uORF$_{AtBRI1}$ on AtBRI1 mRNA translation. More than 30 mutants were obtained, and two of them, each with a 1-nucleotide (G or T) insertion in uATG (FIG. 1*c*), were chosen for further analysis. The AtBRI1 mRNA levels of homozygous lines of the two mutants (uorf$_{AtBRI1}$+g and uorf$_{AtBRI1}$+t, respectively) did not differ substantially from that of WT control, but AtBRI1 protein was increased by approximately 20% higher in uorf$_{AtBRI1}$+g and 90% higher in uorf$_{AtBRI1}$+t (FIG. 1*d*). A previous study has shown that over expression of AtBRI1 could reduce the inhibition of *Arabidopsis* hypocotyl growth by brassinazole (a potent inhibitor of BR biosynthesis)[6]. Consistent with this finding, the hypocotyls of uorf$_{AtBRI1}$+t seedlings were significantly longer than those of WT control in the presence of exogenous brassinazole (FIG. 1*e*).

Figure 4:
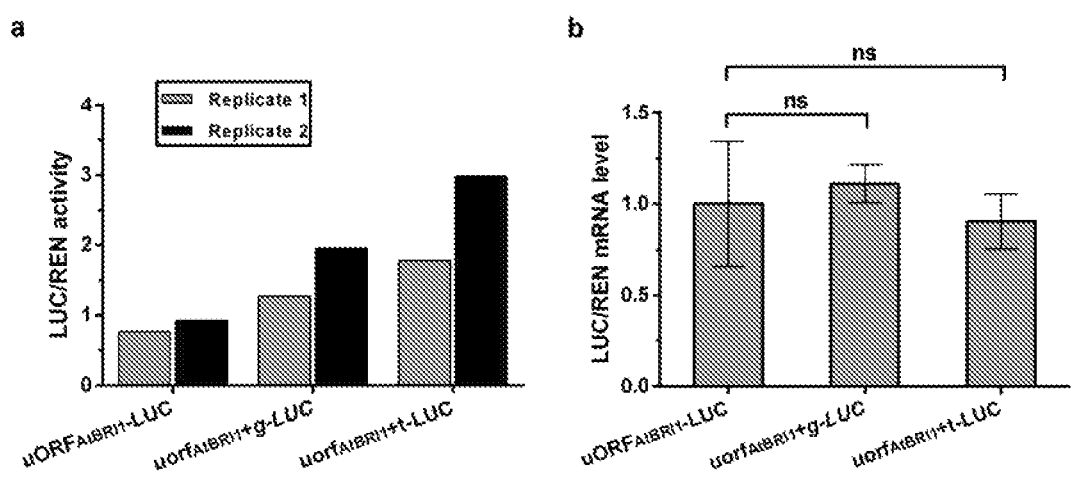
FIG. 4. Effects of WT and mutated uORF sequences of AtBRI1 on the translation and mRNA levels of downstream ORF as investigated using a dual luciferase system. (a) The LUC/REN activity (an indicator of downstream ORF translation) was considerably increased by the uorf sequence in the mutants uorf$_{AtBRI1}$+g or uorf$_{AtBRI1}$+t relative to that conferred by the WT uORF sequence of AtBRI1. Two different experiments (Replicates 1 and 2) were conducted, with similar findings. (b) The LUC/REN mRNA levels did not differ significantly among the three constructs. The means (±SD) were calculated based on three separate assays. ns, no significant difference by two-tailed Student's t-test.

But no obvious difference was observed between the hypocotyls of uorf$_{AtBRI1}$+g and WT seedlings (FIG. 1e). This might be due to lower raise of AtBRI1 protein in uorf$_{AtBRI1}$+g than in uorf$_{AtBRI1}$+t (FIG. 1d). The higher tolerance of uorf$_{AtBRI1}$+t to brassinazole coincided with higher level of AtBRI1 protein (FIG. 1d). Together, these results reveal for the first time the functional role of uORF$_{AtBRI1}$ in controlling AtBRI1 translation in vivo, and prove the idea that disrupting uORF via CRISPR editing can relieve inhibition of translation of the downstream pORF by the uORF. The accumulation of more AtBRI1 in uorf$_{AtBRI1}$+t than in uorf$_{AtBRI1}$+g may be due to greater relief of translation inhibition of pORF in uorf$_{AtBRI1}$+t. In the dual luciferase reporter assay, disruption of uORF$_{AtBRI1}$ by inserting T in uATG also resulted in higher LUC/REN activities than disruption by inserting G (FIG. 4). It is possible that the newly created GTG and TTG in uorf$_{AtBRI1}$+g and uorf$_{AtBRI1}$+t, respectively, allow some residual functioning of uORF$_{AtBRI1}$, with the former retaining greater activity. This reasoning is in line with past studies showing that, GTG and TTG can serve as initiation codons although with lower efficiencies than ATG[8, 9].

Example 3 Identifying uORF$_{AtVTC}$2

Having proven the concept using uORF$_{AtBRI1}$, the inventors next tested if this strategy could be used to enhance a plant trait valuable for human consumption. A conserved uORF has been found in the 5' proximal region of orthologous plant genes encoding GDP-L-galactose phosphorylase (GGP), a major enzyme in ascorbic acid (AsA, also called vitamin C) biosynthesis in plant cells[10]. AsA is an essential nutrient for humans, and much effort has been devoted to increasing AsA content by biotechnological breeding. In Arabidopsis, AtVTC2 encodes the key GGP isozyme, and a uORF (uORF$_{AtVTC2}$, FIG. 3b) is located in its 5'-leader sequence. AsA exerts negative feedback control on AtVTC2 mRNA translation, and the uORF is essential for this feedback control. Due to the lack of plants with mutations in the uORF of AtVTC2, it was not known whether disruption of the uORF would increase AsA content.

There are two putative, noncanonical initiation codons (ATCACG) at the beginning of uORF$_{AtVTC2}$ (FIG. 3b). In two homozygous mutants of uORF$_{AtVTC}$2 that the inventors developed, one (uorf$_{AtVTC2-1}$) carries a 37-nucleotide deletion and removes the adenine residue of the first putative initiation codon ATC, and the other (uorf$_{AtVTC2-2}$), having a 1-nucleotide insertion and 9-nucleotide deletion, destroys both potential initiation codons (FIG. 2a).

Figure 2:
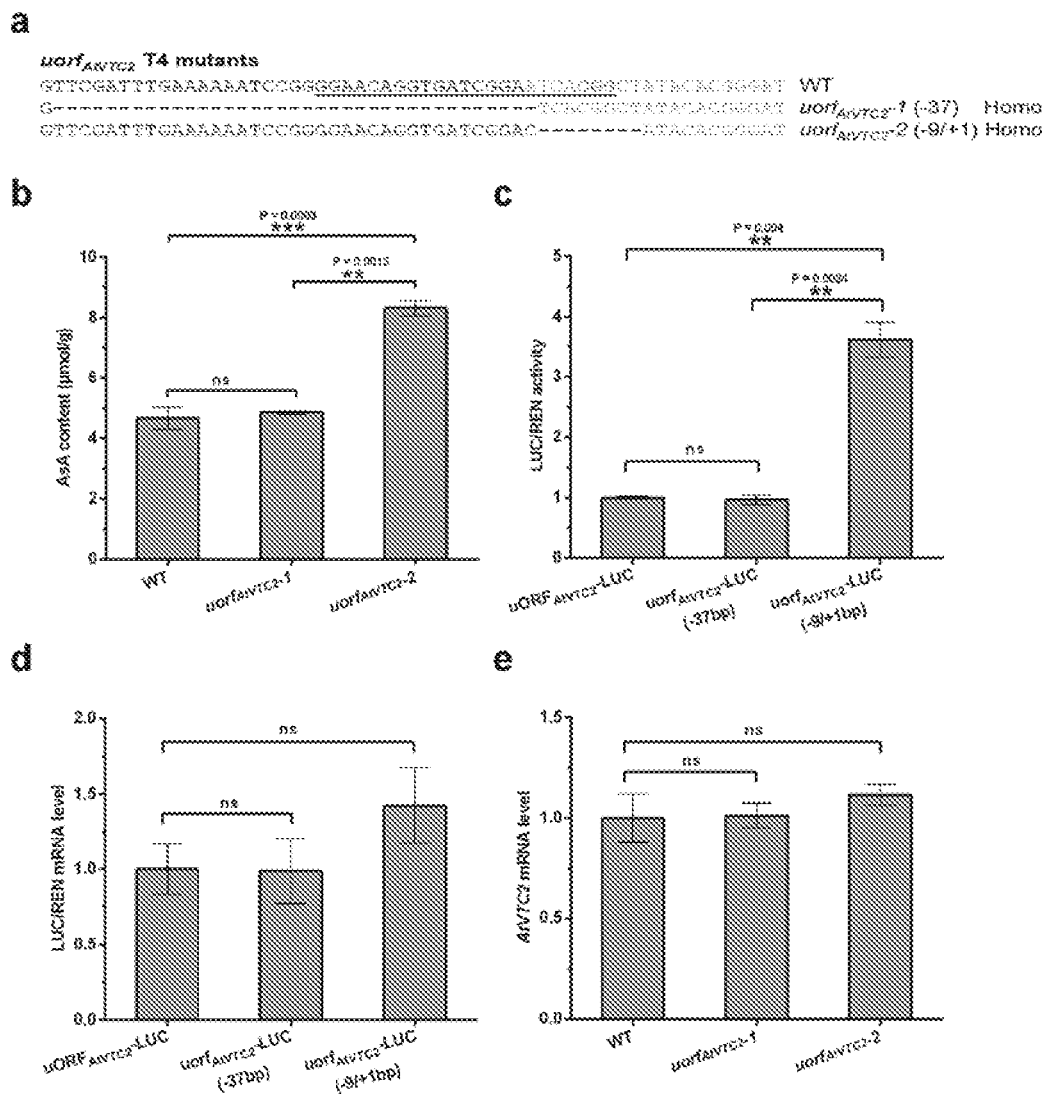
FIG. 2. Disruption of the uORF of AtVTC2 and its effects on AsA content. (a) CRISPR/Cas9 induced sequence changes in the two uORF mutants of AtVTC2. The two mutants carried either a 37-nucleotide deletion (uorf$_{AtVTC2}$-1) or an indel composed of a 1-nucleotide insertion and 9-nucleotide deletion (uorf$_{AtVTC2}$-2). The uORF sequence is labeled blue, the sgRNA targeting sequence is underlined, and the proto-adjacent motif is shown in bold. (b) Comparison of foliar AsA content among WT control and the homozygous mutants uorf$_{AtVTC2}$-1 and uorf$_{AtVTC2}$-2 at T4 generation. The rosette leaves of 14-day-old seedlings were used for AsA assay by HPLC. The mean AsA contents (±SD) shown were each calculated from the measurements of three replicates. (c, d) Effects of WT and mutant uORFs of AtVTC2 on LUC/REN activities (c) and mRNA levels (d) as assessed using the dual luciferase reporter system in the *Arabidopsis* protoplasts incubated for 48 h. uORF$_{AtVTC2}$-LUC, uorf$_{AtVTC2}$-LUC (−37 bp) and uorf$_{AtVTC2}$-LUC (−9/+1 bp) were created by fusing the WT uORF of AtVTC2 and the mutant uorf sequences of uorf$_{AtVTC2}$-1 and uorf$_{AtVTC2}$-2 with LUC coding region, respectively. The mean LUC/REN activity and mRNA levels by uorf$_{AtVTC2}$-LUC (−37 bp) and uorf$_{AtVTC2}$-LUC (−9/+1 bp) were normalized to those of uORF$_{AtVTC2}$-LUC (n=3). (e) Comparison of AtVTC2 mRNA level among WT control and uorf$_{AtVTC2}$-1 and uorf$_{AtVTC2}$-2 by qRT-PCR. *Arabidopsis* Actin2 was used as internal control for the assay (n=3). All values are means±S.D. P<0.01, *P<0.001; ns, no significant difference by two-tailed Student's t-test.

In T4 seedlings, the AsA content of uorf$_{AtVTC2-2}$ was over 70% higher than that of the WT control, whereas no significant difference in AsA content was detected between uorf$_{AtVTC2-1}$ and WT control (FIG. 2b). The latter finding suggested that, in uorf$_{AtVTC2-1}$, the mutant uORF (carrying the −37 bp deletion) with the ACG codon remained and ORF sequence undisturbed may still confer strong inhibition of pORF translation. This was confirmed using the dual luciferase reporter assay (FIG. 2c, d). As anticipated, the mutant uORF in uorf$_{AtVTC2-2}$, which had ATCACG removed, failed to inhibit pORF translation in the same assay (FIG. 2c, d). The mRNA levels of AtVTC2 did not differ significantly in WT control, uorf$_{AtVTC2-1}$ and uorf$_{AtVTC2-2}$ (FIG. 2e), suggesting that the large increase of AsA in uorf$_{AtVTC2-2}$ is caused by increased AtVTC2 mRNA translation. Collectively, these observations show that disruption of uORF$_{AtVTC2}$ increases the production of AtVTC2 protein and hence AsA.

Example 4 Constructing Vegetable Plant with Increased AsA Content

Figure 6:
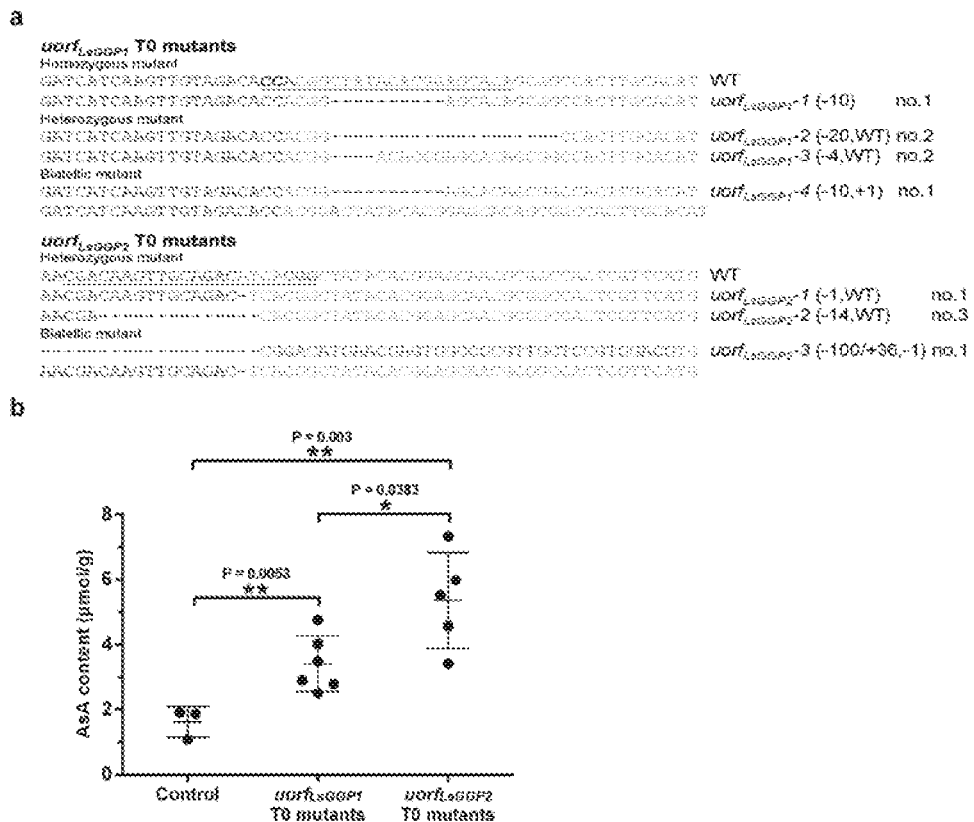
FIG. 6. CRISPR/Cas9 induced mutant uORF alleles of LsGGP1 and LsGGP2 and their AsA contents in leaves in the T0 seedlings. (a) uORF mutant allele of LsGGP1 and LsGGP2 was identified by sequencing the PCR amplicons. WT sequence is provided on top to facilitate the comparison. Note that the T0 seedlings included three types, homozygous, heterozygous, and bi-allelic mutants. The uORFs sequences are colored blue. The sgRNA targeting sequences are underlined, with the PAMs shown in bold. The inserted nucleotides are written in dark red. The no. 1, 2 or 3 means the number of plants in each type of mutants. (b) AsA contents measured for control lettuce seedlings (transformed with the empty vector pKSE401, n=3) and the T0 seedlings carrying the mutant uORF alleles of LsGGP1 (n=6) or LsGGP2 (n=5).

To see if editing the uORF conserved in AtVTC2 orthologs can be used to raise AsA in fresh vegetable plants, which constitute a low-cost and convenient source of AsA, we used lettuce (Lactuca sativa L.), a globally popular vegetable. Two different GGP encoding genes, LsGGP1 and LsGGP2, were found in lettuce, and their deduced products were more than 70% identical to AtVTC2 (FIG. 5). The positions of the uORFs in LsGGP1 (uORF$_{LsGGP1}$) and LsGGP2 (uORF$_{LsGGP2}$) were similar to that of uORF$_{AtVTC2}$ in AtVTC2 (FIG. 3b-d). The putative initiation codons were ACG for uORF$_{LsGGP1}$ and ATCACG for uORF$_{LsGGP2}$ (FIG. 3c, d). Two sgRNAs are used to mutate uORF$_{LsGGP1}$ and uORF$_{LsGGP2}$ (FIG. 6), respectively. For uORF$_{LsGGP1}$, the mutant alleles all retained the ACG codons but with the uORF coding capacity debilitated by indels; in the case of uORFLsGGP2, the mutant alleles either retained only one (ACG) of the two original initiation codons (ATCACG) or had lost both of them (FIG. 6a). The foliar AsA content of individual T0 mutants was assayed, and the data were analyzed with Boxplot. Altering uORF$_{LsGGP1}$ and uORF$_{LsGGP2}$ increased AsA content by 54-194% and 183-352%, respectively (FIG. 6b).

Figure 7:
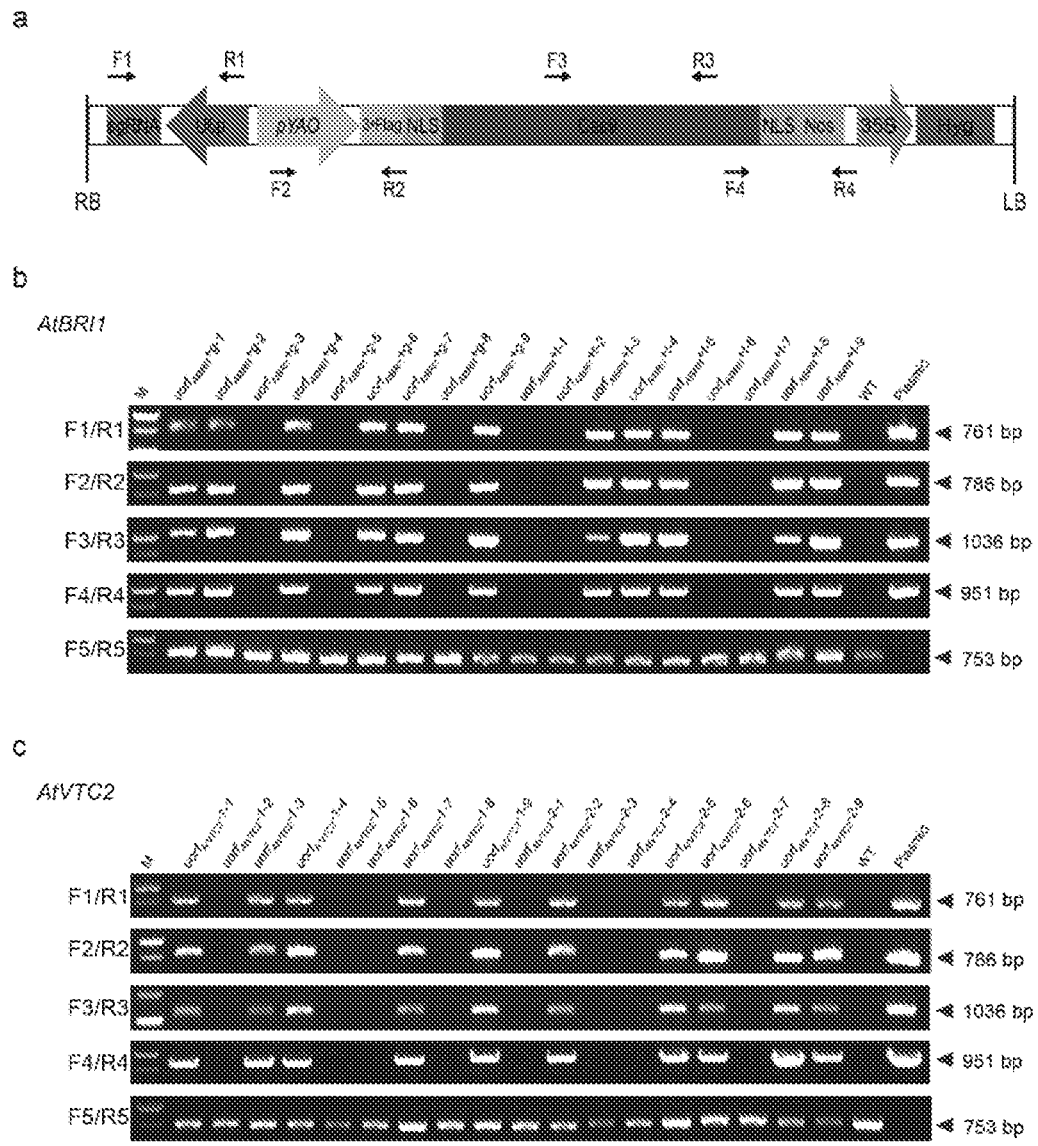
FIG. 7. Detection of transgene-free mutants with four primer sets based on the binary vector. (a) Schematic of the CRISPR/Cas9 binary vector used for transformation by floral dipping. Four pairs of primers indicated by the black arrows were used to detect transgene-free mutants. (b, c) PCR results of transgenic plants. Lanes with no bands generated by the first four pairs of primers indicate transgene-free mutants. F5/R5 was designed to amplify a fragment of AtBRI1 that was used as a control.

These findings clue that genome of uORFs can be used in regulating mRNA translation, which is a widely applicable way to generate genetic diversity for studying key biological processes (e.g., AtBRI1 mediated signaling) and engineering valuable crop traits (e.g. AsA content). Because of the high incidence of uORFs in eukaryotic genes and the development of genome editing methods for an ever greater number of crop species, the potential of our strategy appears to be great. An important advantage of CRISPR-mediated editing is that uORF mutants can be made transgene-free by segregation or by employing DNA-free editing methods[14-16]. By analyzing segregating populations via PCR, transgene-free progenies of AtBRI1 and AtVTC2 uORF mutants have been readily obtained (FIG. 7 and Table 3).

TABLE 3

Segregation analysis of hygromycin sensitivity of T4 generation of uorf$_{AtBRI1}$ and uorf$_{AtVTC2}$ mutants.

| Gene name | Mutant name | Total number of tested T4 seedlings | Number of hygro-mycin-sensitive seedlings | Number of hygro-mycin-resistant seedlings | Frequency of trans-gene-free seedlings (%) |
|---|---|---|---|---|---|
| AtBRI1 | uorf$_{AtBRI1}$ + g | 44 | 12 | 32 | 27.3 |
| | uorf$_{AtBRI1}$ + t | 46 | 11 | 35 | 23.9 |
| AtVTC2 | uorf$_{AtVTC2}$ − 1 | 48 | 8 | 40 | 16.7 |
| | uorf$_{AtVTC2}$ − 2 | 65 | 15 | 50 | 23.1 |

Example 5 Generating uORFs for Other Target Genes

To see whether the method for regulating gene expression can be widely used, uORFs have been created for five more different target genes.

For CHLH, the construct with CHLH-C-Tm generated about 20% LUC/REN activities of the construct with CHLH-WT (FIG. 9a), while the construct with CHLH-C-Am generated about 75% LUC/REN activities of the construct with CHLH-WT (FIG. 9a). These results suggest that LUC translation is markedly inhibited by the presence of the mutated form CHLH (with a newly generated uORF), the mutation of which can substantially reduce the translation of downstream pORF. Alterations in CHLH translation effect chlorophyll synthesis, when T-DNA simultaneously (homozygous) disrupts the function of the gene, causing albino seedlings (FIG. 9).

Figure 10:
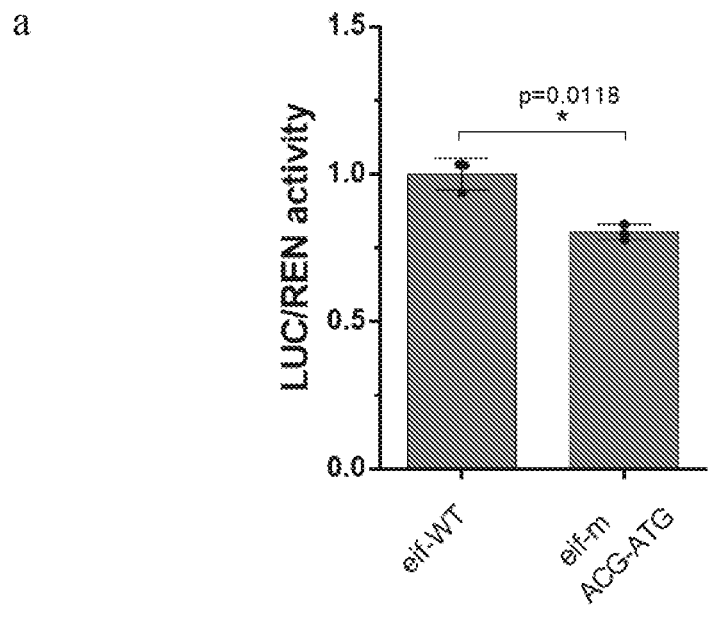
FIG. 10. Genome editing of the uORF of Eukaryotic initiation factor iso-4F to reduce the translation of Eukaryotic initiation factor iso-4F. (a) Effects of WT and mutant uORFs of Eukaryotic initiation factor iso-4F on LUC/REN activities as assessed using the dual luciferase reporter system. eif-m differed from eif-WT by the mutation of ACG to ATG. The mean LUC/REN activity conferred by eif-m-LUC were normalized to those of eif-WT-LUC (n=3). (b) The 5'-leader sequence of Eukaryotic initiation factor iso-4F. The potential uORF is underlined. This 5'-leader sequence contains 1 potential uORF, ACG→ATG(eif-m ACG-ATG).

For Eukaryotic initiation factor iso-4F, the construct with eif-m generated about 75% LUC/REN activities of the construct with eif-WT (FIG. 10a). These results suggest that LUC translation is markedly inhibited by the presence of the mutated form Eukaryotic initiation factor iso-4F (with a newly generated uORF), the mutation of which can substantially reduce the translation of downstream pORF. Alterations in Eukaryotic initiation factor iso-4F expression may provide resistance to specific virus (FIG. 10).

For Cytochrome P450 gene, the construct with CYTO-m generated about 75% LUC/REN activities of the construct with CYTO-WT (FIG. 11a). These results suggest that LUC translation is markedly inhibited by the presence of the mutated form Cytochrome P450 gene (with a newly generated uORF), the mutation of which can substantially reduce the translation of downstream pORF. Alterations in Cytochrome P450 expression make seedlings more sensitive to herbicides (bensulfuron-methyl (BSM)), showing slow growth (FIG. 11).

For SPINDLY gene, the construct with SPY-1C-Tm generated about 75% LUC/REN activities of the construct with SPY-WT (FIG. 12*a*), while the construct with SPY-2C-Tm generated about 5% LUC/REN activities of the construct with SPY-WT (FIG. 12*a*). These results suggest that LUC translation is markedly inhibited by the presence of the mutated form SPINDLY gene (with a newly generated uORF), the mutation of which can substantially reduce the translation of downstream pORF. Alterations in SPINDLY expression increase internode growth during vegetative growth (FIG. 12).

For PHOTOPERIOD SENSITIVITY 5 (SE5) gene, the construct with SE5-1C-Tm generated about 90% LUC/REN activities of the construct with SE5-WT (FIG. 13*a*), while the construct with SE5-2C-Tm generated about 15% LUC/REN activities of the construct with SE5-WT (FIG. 13*a*). These results suggest that LUC translation is markedly inhibited by the presence of the mutated form SE5 gene (with a newly generated uORF), the mutation of which can substantially reduce the translation of downstream pORF. Alterations in SE5 translation show early flowering under long-day conditions (FIG. 13).

REFERENCES

1. Schwanhausscr, B. et al. *Nature.* 473, 337-342 (2011).
2. Calvoa, S. E. Pagliarinia, D. J. & Moothaa, V. K. *Proc. Nat. Acad. Sci. U.S.A.* 106, 7507-12 (2009).
3. von Arnim, A. G, Jia, Q. & Vaughn, J. N. *Plant Sci.* 214, 1-12 (2014).
4. Liang X. H. et al. *Nat Biotechnol.* 34, 875-882 (2017).
5. Xu, G. et al. *Nature.* 545, 487-490 (2017).
6. Wang, Z. Y. et al. *Nature.* 410, 380-383 (2001).
7. Hellens, R. P. et al. *Plant Methods.* 1, 13 (2005).
8. Kawakami, T. et al. *Microbiol Immunol.* 43, 351-357 (1999).
9. Mehdi, H., Ono, E. & Gupta, K. C. *Gene.* 91:173-178 (1990).
10. Laing, W. A. et al. *Plant Cell.* 27, 772-786 (2015).
11. Buley, S. M. et al. *Plant Biotechnol. J.* 10, 390-397 (2012).
12. Zhou, Y. et al. *Biol. Plant.* 56, 451-457 (2012).
13. Reyes-Chin-Wo, S. et al. *Nat Commun.* 8.14953 (2017).
14. Woo, J. W. et al. *Nat Biotechnol.* 33, 1162-1164 (2015).
15. Zhang, Y et al. *Nat Commun.* 7, 12617 (2016).
16. Liang, Z. et al. *Nat Conunun.* 8, 14261 (2017).
17. Yan, L. et al. *Mol Plant.* 8, 1820-1823 (2015).
18. Xing, H. L. et al. *BMC Plant Biol.* 14, 327 (2014).
19. Hellens, R. P. et al. *Plant Methods.* 1, 13 (2005).
20. Zhai, Z., Jung, H. I. & Vatamaniuk, O. K. et al. *J Vis Exp.* 30, pii: 1149. doi: 10.3791/1149 (2009).
21. Yoo, S. D., Cho, Y. H. & Sheen, *J. Nat Protoc.* 2:1565-1572 (2007).
22. Cui, F. et al. *Plant Cell* 24, 233-244 (2012).
23. Zhang, H. et al. *Plant cell.* 27, 214-227 (2015).
24. Kovacs, L. et al. *Bio-protocol.* 6, e2067 (2016).

The invention claimed is:

1. A method for regulating expression of a target protein in a plant cell, wherein the 5' untranslated region (5'-UTR) of the encoding gene of said target protein comprises an upstream open reading frame (uORF), wherein the method comprises introducing into the plant cell a genome editing system that targets the uORF, thereby increasing or decreasing or eliminating inhibition of target protein expression by the uORF,
wherein the introduction of the genome editing system that targets the uORF results in mutation of one or more nucleotides in the uORF, and
wherein
(i) the mutation of one or more nucleotides results in a weak translation initiation codon in the uORF being mutated into a strong translation initiation codon, whereby inhibition of target protein expression by the uORF is enhanced and target protein expression level is reduced, or
(ii) the mutation of one or more nucleotides results in a strong translation initiation codon in the uORF being mutated into a weak translation initiation codon, or the mutation results in the uORF not being translated, whereby inhibition of target protein expression by the uORF is reduced and target protein expression level is increased, and
wherein the strong translation initiation codon is ATG, and the weak translation initiation codon is selected from the group consisting of GTG, ATC, ACG, TTG or AAG.

2. The method of claim 1, wherein the genome editing system is selected from the group consisting of a precise base editing (PBE) system, a CRISPR-Cas9 system, a CRISPR-Cpf1 system, a CRISPRi system, a zinc finger nuclease system, and TALEN system.

3. The method of claim 1, wherein the plant cell is a cell of plants including monocots and dicots, such as a cell of rice, corn, wheat, sorghum, barley, soybean, peanut, *Arabidopsis thaliana, Lactuca sativa*.

4. A plant cell engineered by the method of claim 1, wherein the expression level of the target protein in the plant cell is altered relative to an unmodified plant cell.

5. A method of producing a genetically modified plant, comprising the step of regenerating an intact plant from the cell of claim 4, wherein the expression level of the target protein in the genetically modified plant is altered relative to a plant that has not been genetically modified.

* * * * *